(12) United States Patent
Zheng et al.

(10) Patent No.: US 10,793,617 B2
(45) Date of Patent: *Oct. 6, 2020

(54) METHODS OF USE OF SOLUBLE CD24 FOR THERAPY OF RHEUMATOID ARTHRITIS

(71) Applicant: OncoImmune, Inc., Rockville, MD (US)

(72) Inventors: Xincheng Zheng, Ann Arbor, MI (US); Wei Wu, Washington, DC (US); Yang Liu, Washington, DC (US); Pan Zheng, Washington, DC (US)

(73) Assignee: ONCOIMMUNE, INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/104,072

(22) Filed: Aug. 16, 2018

(65) Prior Publication Data

US 2019/0016783 A1 Jan. 17, 2019

Related U.S. Application Data

(63) Continuation of application No. 15/437,968, filed on Feb. 21, 2017, now abandoned, which is a continuation of application No. 14/519,745, filed on Oct. 21, 2014, now Pat. No. 9,611,309, which is a continuation of application No. 14/055,609, filed on Oct. 16, 2013, now Pat. No. 8,895,022, which is a continuation of application No. 13/892,705, filed on May 13, 2013, now abandoned, which is a continuation-in-part of application No. 13/643,527, filed as application No. PCT/US2011/034282 on Apr. 28, 2011, now Pat. No. 8,808,697.

(60) Provisional application No. 61/329,078, filed on Apr. 28, 2010.

(51) Int. Cl.
| | |
|---|---|
| *C07K 16/46* | (2006.01) |
| *C07K 14/47* | (2006.01) |
| *C07K 14/00* | (2006.01) |
| *A61K 45/06* | (2006.01) |
| *A61K 38/00* | (2006.01) |
| *C07K 14/705* | (2006.01) |
| *C07K 14/435* | (2006.01) |
| *C07K 19/00* | (2006.01) |

(52) U.S. Cl.
CPC ...... *C07K 14/70596* (2013.01); *C07K 14/435* (2013.01); *C07K 14/47* (2013.01); *C07K 19/00* (2013.01); *C07K 2319/30* (2013.01)

(58) Field of Classification Search
CPC ...... C07K 16/46; C07K 14/00; C07K 14/705; C07K 14/435; C07K 14/70596; C07K 19/00; C07K 14/47; C07K 2319/30; A61K 38/177; A61K 45/06; A61K 31/351
See application file for complete search history.

(56) References Cited

U.S. PATENT DOCUMENTS

| | | | |
|---|---|---|---|
| 5,726,044 | A | 3/1998 | Lo |
| 6,280,732 | B1 | 8/2001 | Caras |
| 7,744,894 | B2 | 6/2010 | Liu et al. |
| 7,794,718 | B2 | 9/2010 | Karrer |
| 2003/0106084 | A1 | 1/2003 | Liu et al. |
| 2003/0095966 | A1 | 5/2003 | Liu et al. |
| 2006/0160220 | A1 | 7/2006 | Bremel |
| 2008/0267980 | A1 | 10/2008 | Tomlinson et al. |
| 2009/0011407 | A1 | 1/2009 | Liu |
| 2014/0107322 | A1 | 4/2014 | Zheng |
| 2015/0239953 | A1 | 8/2015 | Zheng et al. |

FOREIGN PATENT DOCUMENTS

| | | |
|---|---|---|
| CN | 101125888 A | 2/2008 |
| WO | 2011/139820 | 11/2011 |
| WO | 2018/213266 A1 | 11/2018 |

OTHER PUBLICATIONS

Yu et al., Autoimmune Reviews 17: 473-479 (Year: 2018).*
Toubal, T., et al., "Siglec-G-CD24 Axis Controls the Severity of Graft-Versus Host Disease in Mice," Blood, vol. 123, No. 22, pp. 3512-3523 (May 29, 2014).
Toubal, T., et al., CD24-Siglec-G Interaction Plays an Important in Reducing Eperimental Graft-versus-host Disease (GVHD), Blood, vol. 120, No. 21, p. 453 (Nov. 16, 2012).
Ziemssen, T., et al., "The Role of the Humoral Immune System in MultpleSclerosis (MS) and its Animal Model Experimental Autoimmune Encephalomyelitis (EAE)" Autoimmunity Reviews, vol. 4, pp. 460-467 (May 11, 2005).

\* cited by examiner

*Primary Examiner* — Phuong Huynh
(74) *Attorney, Agent, or Firm* — Polsinelli PC; Ron Galant

(57) ABSTRACT

Provided herein is a CD24 protein. The CD24 protein may include mature human or mouse CD24, as well as a N- or C-terminally fused portion of a mammalian immunoglobulin.

14 Claims, 20 Drawing Sheets
Specification includes a Sequence Listing.

Fig. 1A

MGRAMVARLGLGLLLLALLLPTQIYSSETTTGTSSNSSQSTSNSGLAP
NPTNATTKPKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

Fig. 1B

MGRAMVARLGLGLLLLALLLPTQIYSSETTTGTSSNSSQSTSNSGLAP
NPTNATTKVPKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 3

```
Mouse cd24   NQTSVAPFPGN--QNISAS----PNPTNATTRG
             -*  -      *  * **     ********--
Human CD24   SETTTGTSS-NSSQSTSNS-GLAPNPTNATTKA(V)
```

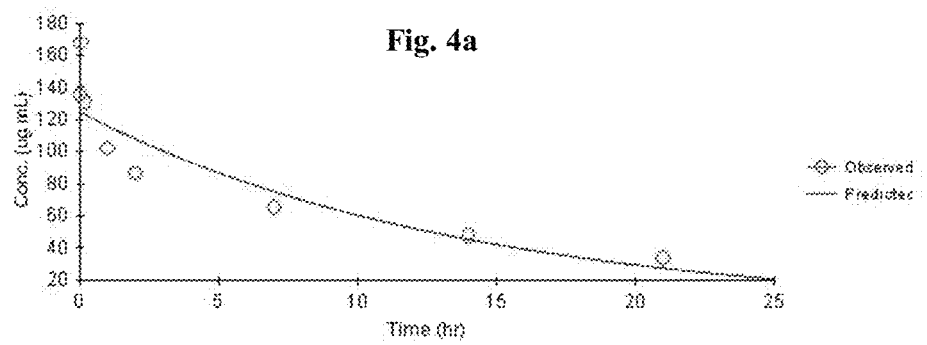
Fig. 4a
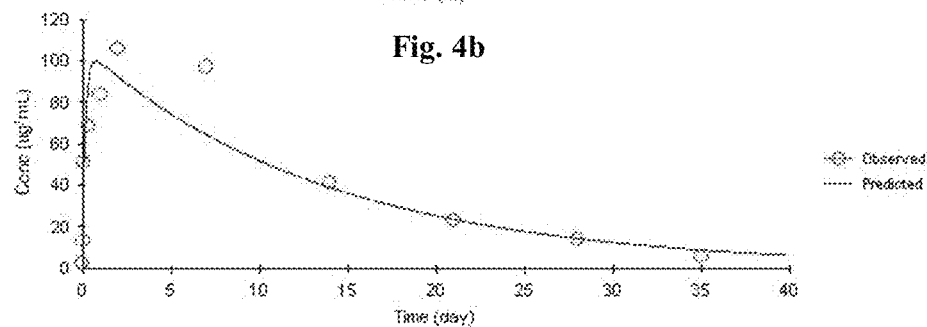
Fig. 4b
Fig. 4c
| Routes | Parameter | Units | Estimate | StdError | CV% |
|---|---|---|---|---|---|
| i.v. | AUC | day*ug/mL | 1709.5 | 305.2 | 17.85 |
| s.c. | | | 1453.2 | 181.4 | 12.49 |
| i.v. | K10_HL | day | 9.52 | 1.96 | 20.56 |
| s.c. | | | 9.54 | 1.43 | 14.97 |
| i.v. | Cmax | ug/mL | 124.4 | 10.3 | 8.31 |
| s.c. | | | 99.8 | 11.1 | 11.11 |

The dose dependant therapeutic effect of CD24Fc

Fisher PLSD $P=0.02$

Fisher PLSD $P=0.02$

Days after the first immunization

Days after immunization

METHODS OF USE OF SOLUBLE CD24 FOR THERAPY OF RHEUMATOID ARTHRITIS

FIELD OF THE INVENTION

This invention relates to compositions and methods for treating rheumatoid arthritis.

REFERENCE TO THE SEQUENCE LISTING

Applicant hereby makes reference to the Sequence Listing that is contained in the file "060275-0400-06USCN-Sequence-Listing.txt" (9 kB; created on Aug. 8, 2018), the contents of which are incorporated herein by reference.

BACKGROUND OF THE INVENTION

This section provides background information which is not necessarily prior art and a general summary of the present disclosure which is not a comprehensive disclosure of its full scope or all of its features.

CD24 is known as the heat-stable antigen. It is expressed as a glycosyl-phosphatidyl-inositol (GPI)-anchored molecule and has a wide distribution in different lineages. Because of the tendency of CD24 to be expressed on immature cells, it has also been used as part of stem cell markers and for lymphocyte differentiation. The first function associated with CD24 is a costimulatory activity for antigen-specific T cell response. In vivo studies indicated that, as a costimulator for T cell activation in the lymphoid organ, CD24 is redundant but becomes essential in the absence of CD28. This would not be the case for local target organs that are not as "costimulator rich." Consistent with this notion, it has been demonstrated that mice with a targeted mutation of CD24 are completely resistant to induction of experimental autoimmune encephalomyelitis (EAE).

Polymorphisms of human CD24 are associated with risk and progression of several autoimmune diseases, including multiple sclerosis and rheumatoid arthritis (RA). In cases of multiple sclerosis, it has been reported that soluble CD24, consisting of the extracellular portion of murine CD24 and human IgG1 Fc ameliorated the clinical symptom of experimental autoimmune diseases, the mouse model of multiple sclerosis. More recent studies have demonstrated that CD24 interact with and represses host response to danger-associated molecular patterns (DAMPs).

RA affects 0.5-1% of human populations. Although a number of disease-modifying antirheumatic drugs (DMARDs) are currently available, even the gold standard of biologic DMARDs, the therapeutics targeting the tumor-necrosis factor alpha, lead to 50% improvement according to American College of Rheumatology Improvement Criteria (ACR50) in less than 50% of the patients receiving the treatments. No cure for RA is available. It is therefore necessary to test additional therapeutics for RA. RA is presumed to be autoimmune diseases in the joint, although the cause of the diseases remains largely obscure. A number of studies have implicated T cells in the pathogenesis of rheumatoid arthritis. More recently, it has been demonstrated that transfer of antibodies can cause the development of inflammation of the joints of mice. The pathology of the lesions resembles human rheumatoid arthritis.

Animal models relevant to human RA played an important role for the advancement of therapeutic development in DMARDs. For example, collagen-induced arthritis in the mouse and rat were critical for the development of therapeutics for RA. More recently, it has been demonstrated that adaptive transfer of anti-collagen antibodies cause robust RA-like lesion in the mice. Since auto-antibodies are elevated in RA patients prior to the onset of diseases, passive transfer of collagen-specific antibody is a relevant model for human RA.

Since the pathogenesis of RA involves host response to DAMP and since the CD24 molecule negatively regulate host response to DAMPs, the potential of using soluble CD24 to treat RA was investigated. The passive transfer model of RA was chosen because of both relevance to human diseases and simplicity of experimental designs.

SUMMARY OF THE INVENTION

Provided herein is a CD24 protein comprising a mature human CD24 variant consisting of SEQ ID NO: 1. The CD24 protein may further comprise a portion of a mammalian immunoglobulin (Ig), which may be fused to the N-terminus or C-terminus of the mature CD24. The Ig portion may be the Fc portion of a human Ig protein. The Fc portion may consist of the hinge region and CH2 and CH3 domains of the human Ig protein, and the Ig may be IgG1, IgG2, IgG3, IgG4, or IgA. The Fc portion may consist of the hinge region and CH3 and CH4 regions of IgM.

The CD24 protein may be soluble, and may be glycosylated. The CD24 protein may also be produced using a eukaryotic protein expression system, which may comprise a vector contained in a Chinese Hamster Ovary cell line or a replication-defective retroviral vector. The replication-defective retroviral vector may be stably integrated into the genome of a eukaryotic cell.

BRIEF DESCRIPTION OF THE DRAWINGS

FIGS. 1A-B. FIG. 1A shows the amino acid composition of the CD24 fusion protein, CD24IgG1Fc (also referred to herein as CD24Fc) (SEQ ID NO: 5). The underlined 26 amino acids are the signal peptide of CD24 (SEQ ID NO: 4). The boxed, bold portion of the sequence is the mature CD24 protein used in the fusion protein (SEQ ID NO: 1). The last amino acid (A or V) that is ordinarily present in the mature CD24 protein has been deleted from the construct to avoid immunogenicity. The non-underlined, non-bold letters are the sequence of IgG1 Fc, including the hinge region and CH1 and CH2 domains (SEQ ID NO: 6). FIG. 1B shows the sequence of CD24$^V$Fc (SEQ ID NO: 7), in which the mature human CD24 protein is the valine polymorphic variant of SEQ ID NO: 2. The various parts of the fusion protein are marked as in FIG. 1A.

FIG. 3. Amino acid sequence variations between mature CD24 proteins from mouse (SEQ ID NO: 3) and human (SEQ ID NO: 2). The potential glycosylation sites are bolded, with the N-glycosylation sites in red.

FIGS. 4A-C. WinNonlin compartmental modeling analysis of pharmacokenitics of CD24IgG1 (CD24Fc). The opened circles represent the average of 3 mice, and the line is the predicted pharmacokinetic curve. FIG. 4A. i.v. injection of 1 mg CD24IgG1. FIG. 4B. s.c. injection of 1 mg CD24IgG1 (CD24Fc). FIG. 4C. Comparison of the total amounts of antibody in the blood as measured by areas under curve (AUC), half-life and maximal blood concentration. Note that overall, the AUC and Cmax of the s.c. injection is about 80% of i.v. injection, although the difference is not statistically significant.

FIG. 5A. Host response to PAMP was unaffected by CD24-Siglec G(10) interaction. FIG. 5B. CD24-Siglec G (10) interaction represses host response to DAMP, possibly through the Siglec G/10-associated SHP-1.

FIG. 6A. Diagram of experiments. BALB/c mice (8 weeks old) received mAbs on day 1 in conjunction with either vehicle or fusion proteins. The mice were injected LPS on day 3, and were observed daily for 3 weeks. FIG. 6B. CD24Fc reduces clinical scores of CAIA. The fusion proteins (1 mg/mouse) or vehicles were injected once on day 1. Clinical scores were determined double blind. *, P<0.05; , P<0.01; *, P<0.001. The effect of CD24 was reproduced in 6 independent experiments, involving a total of 52 mice in the PBS group and 54 mice in CD24Fc group.

FIG. 7A. Representative FACS profile. FIG. 7B. The summary of reduced cytokines (Mean±SE) measured in the joint homogenates.

FIG. 10A. Diagram of experiments. FIG. 10B. Clinical scores of arthritis, scored double blind.

FIG. 12A. Diagram of the fusion proteins. The polymorphic residue in extracellular domain was deleted in CD24Fc. FIG. 12B. SDS-PAGE analysis for the purity of the two fusion proteins. The numbers shown are µg of proteins loaded. FIG. 12C. Comparison between CD24'Fc and CD24Fc for their binding to Siglec10Fc. Desialylated CD24Fc was used as a negative control. FIG. 12D. Comparison between CD24Fc and CD24'Fc for the therapeutic effect in the CAIA model. CD24Fc or CD24'Fc (200 m/mouse) was injected into mice in conjunction with a cocktail of anti-collagen antibodies on day 1. Arthritis was elicited by treatment with LPS on day 3. The diseases were scored double blind. Data shown in FIGS. 12C and D are means and SEM. FIGS. 12E and 12F also compare the therapeutic effects of CD24Fc and CD24$^V$Fc, in experiments performed similarly to the ones shown in FIG. 12D, except that IgG1 Fc was used as a negative control. As shown in FIG. 12E, CD24Fc reduced the RA score as early as day 4, and showed statistically significant protection throughout the three weeks of observation. On the other hand, as shown in FIG. 12F, CD24$^V$Fc showed a reduction in RA score starting on day 8. Although reduced scores were observed thereafter, the reduction did not reach statistical significance.

FIG. 13A. CD24Fc suppressed development of arthritis in the CIA model. Mice received a single treatment (1 mg/mouse) on day 17 when no clinical symptoms had developed. Data shown are disease scores among the mice that had developed arthritis with disease scores from 3 to 8. The difference between CD24Fc and PBS group was significant (P=0.02, Fisher's PLSD test). N=9 for vehicle and N=7 for CD24Fc group. FIG. 13B. Therapeutic effect of CD24Fc in CIA of DBA/1 mice. The mice with clinical symptoms of scores from 3 to 8 were randomized to receive either 200 µg CD24Fc or an equal volume of control vehicle (PBS) by i.p. injection, every the other day, five times. The mice were inspected daily to score for the clinical symptoms for two weeks. CD24Fc significantly lessened the clinical symptoms of arthritis when arthritis developed (P=0.02, Fisher's PLSD test). N=6 for PBS and N=5 for CD24Fc groups.

FIG. 14A. On day 28, mice with a clinical score >3 were randomized to receive either vehicle or CD24Fc (1 mg/mouse). The endpoint was a reduction of score by 50% (top) or 80% (bottom). N=12 for PBS, and N=11 for CD24Fc. FIG. 14B. Dose-dependent therapeutic effect of CD24Fc in chicken CIA model. Details as in FIG. 14A, except that the treatments started at the peak of disease (average score of 5.5 in both groups on day 33). Mice with a clinical score >3 were randomized to receive 5 injections of either vehicle or CD24Fc. The endpoint was a reduction of score by either 50% (top) or 80% (bottom). N=11. The difference between the 100 µg experimental and the vehicle control groups was statistically significant.

FIG. 15A. ShRNA silencing of CD24 led to spontaneous production of TNFα, IL-6 and IL-1β. THP1 cells were transduced with lentiviral vectors encoding either scrambled or two independent CD24 shRNA. The transduced cells were differentiated into macrophages by culturing for 4 days with PMA (15 ng/ml). After washing away PMA and nonadherent cells, the cells were cultured for another 24 hours for measurement of inflammatory cytokines by cytokine beads array. FIG. 15B. As in FIG. 15A, except that the given concentration of CD24Fc or control IgG Fc was added to macrophages in the last 24 hours. FIG. 15C. CD24Fc was more efficient than CD24'Fc in suppressing the spontaneous production of inflammatory cytokines by CD24-silenced macrophage cell line THP1. The data shown are as detailed in the FIG. 12 legends, except that the CD24Fc and CD24'Fc are compared side-by-side.

FIG. 16A. CD24Fc stimulated tyrosine phosphorylation of, and SHP-1 binding to, Siglec G. Spleen cells from CD24-deficient mice were stimulated with either vehicle, Fc control or CD24Fc (1 µg/ml) for 30 min. After lysis, the Siglec G protein was precipitated with anti-Siglec G antisera. Siglec G phosphorylation and its association to SHP-1 were detected by Western blot. FIG. 16B. Siglecg was essential for therapeutic effect of CD24Fc in mice with low dose of anti-collagen antibodies. WT (FIG. 16A) and Siglecg$^{-/-}$ mice (FIG. 16B) received either vehicle control or CD24Fc in conjunction of a cocktail of anti-collagen mAbs (2 mg/mouse). LPS was injected on day 3 (100 µg/mouse). The clinical scores were recorded daily double blind. Data are representative of two experiments. FIG. 16C. Targeted mutation of Siglecg attenuated but did not abrogate the therapeutic effect of CD24Fc with double doses of anti-collagen antibodies. The anti-collagen antibodies (4 mg/mouse) and CD24Fc (1 mg/mouse) were added on day 1, while LPS (100 µg/mouse) was added on day 3. Male WT (FIG. 16A) and Siglecg$^{-/-}$ mice (FIG. 16B) were observed daily for clinical score. % inhibitions were calculated by % reduction of accumulated RA score. N=5. Male mice were used at 8 weeks of age.

FIGS. 17A and B show pharmacokinetic profiles of CD24 in male and female mice at doses of 12.5, 35, and 125 mg/kg.

DETAILED DESCRIPTION

Figure 2:
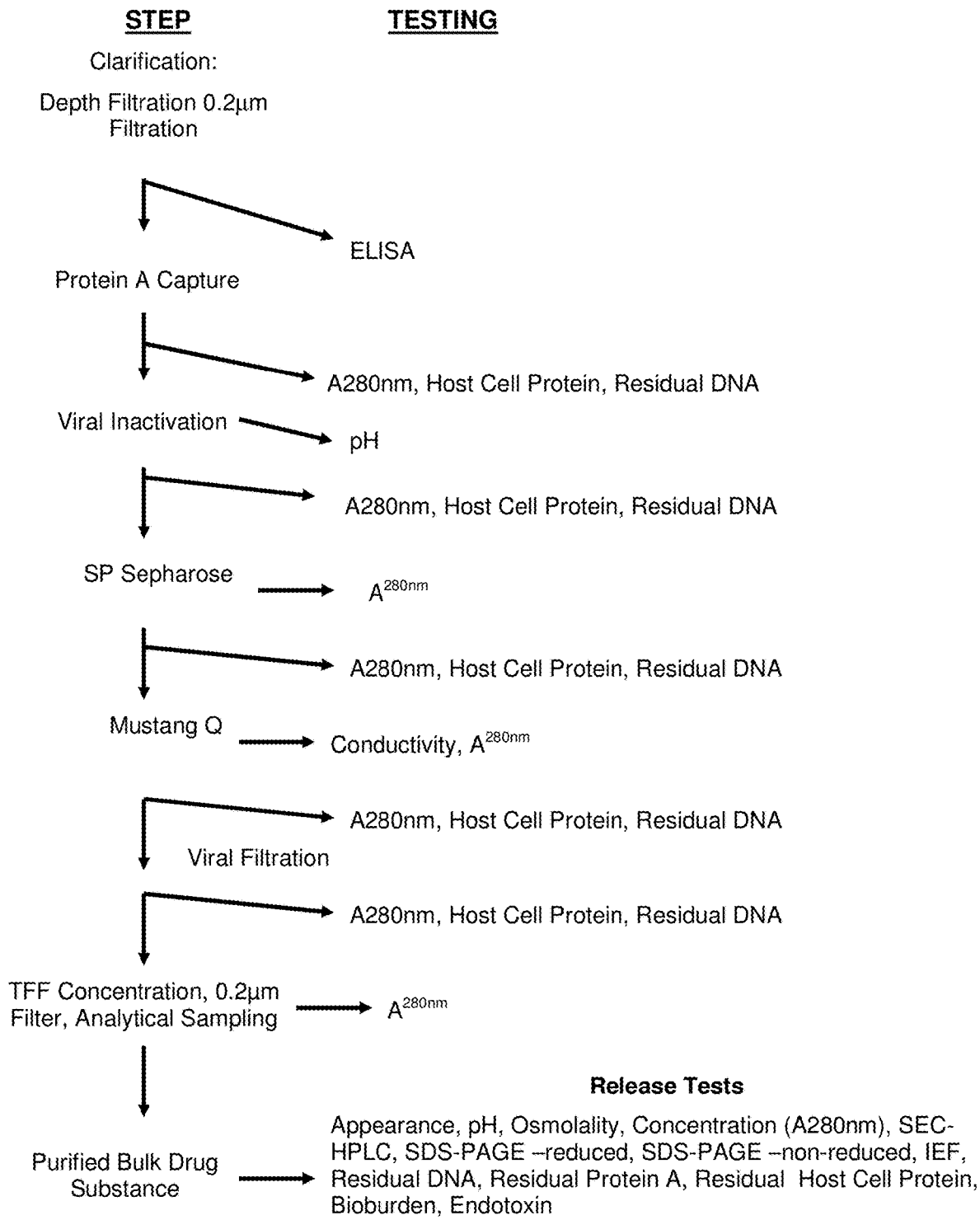
FIG. 2. Methods for purification and processing of CD24IgG1Fc (CD24Fc) expressed from mammalian cell lines.

The inventors have discovered that a soluble form of CD24 is highly effective for treating rheumatoid arthritis. In particular, the inventors have discovered that a variant CD24 fusion protein in which the core of human CD24 lacks the polymorphic amino acid at position 57 of full-length CD24 has a superior therapeutic effect when compared with a CD24 protein which has a wild-type core CD24 sequence.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A "peptide" or "polypeptide" is a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

A "variant" may mean means a peptide or polypeptide that differs in amino acid sequence by the insertion, deletion, or conservative substitution of amino acids, but retain at least one biological activity. Representative examples of "biological activity" include the ability to bind to a toll-like receptor and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. CD24

Provided herein is a CD24 protein, which may have the amino sequence of mature human CD24, which may be SETTTGTSSNSSQSTSNSGLAPNPTNATTK (SEQ ID NO: 1) or SETTTGTSSNSSQSTSNSGLAPNPTNATTK (V/A) (SEQ ID NO: 2), or mouse CD24, which may be NQTSVAPFPGNQNISASPNPTNATTRG (SEQ ID NO: 3), or a variant thereof. The CD24 may be soluble. The CD24 may further comprise a N-terminal signal peptide, which may have the amino acid sequence MGRAMVARLGL-GLLLLALLLPTQIYS (SEQ ID NO: 4). The CD24 may also have an amino acid sequence described in FIG. 1 or 3. The CD24 may exist in one of two allelic forms, such that the C-terminal amino acid of the mature human CD24 may be a valine or an alanine. The C-terminal valine or alanine may be immunogenic and may be omitted from the CD24 to reduce its immunogenicity. The difference between the two alleles may affect the risk of autoimmune diseases, including multiple sclerosis and RA. Nevertheless, since the two allelic forms affect the expression levels of membrane-bounded form, the variation should not affect the function of CD24.

Despite considerable sequence variations in the amino acid sequence of the mature CD24 proteins from mouse and human, they are functionally equivalents in interaction with the danger-associated molecular patterns (DAMP). Since host response to DAMP is considered important for the pathogenesis of RA, the mouse and human CD24 may be functionally equivalent in treating RA. As a result of sequence conservation between mouse and human CD24 primarily in the C-terminus and in the abundance of glycosylation sites, significant variations in the mature CD24 proteins may be tolerated in using the CD24 to treat RA, especially if those variations do not affect the conserved residues in the C-terminus or do not affect the glycosylation sites from either mouse or human CD24.

a. Fusion

The CD24 may be fused at its N- or C-terminal end to a portion of a mammalian Ig protein, which may be human or mouse. The portion may be a Fc region of the Ig protein. The Fc region may comprise the hinge region and CH2 and CH3 domains of the Ig protein. The Ig protein may be human IgG1, IgG2, IgG3, IgG4, IgM, or IgA. The Fc portion may comprise SEQ ID NO: 6. The Ig protein may also be IgM, and the Fc portion may comprise the hinge region and CH3 and CH4 domains of IgM. The CD24 may also be fused at its N- or C-terminus to a protein tag, which may be GST, His, or FLAG. Methods for making fusion proteins and purifying fusion proteins are well known in the art.

b. Production

The CD24 may be heavily glycosylated, and may be involved in functions of CD24 such as costimulation and interaction with danger-associated molecular patterns. The CD24 may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The CD24 may also be produced from a stable cell line that expresses CD24 from a vector or a portion of a vector that has been integrated into the cellular genome. The stable cell line may express CD24 from an integrated replication-defective retroviral vector. The expression system may be GPEx™.

3. Method of Treatment

The CD24 may be used to treat rheumatoid arthritis. The CD24 may be administered to a subject in need thereof. The subject may be a mammal such as a human.

a. Combined CD24 Therapy

The CD24 may be combined with another drug, such as a disease-modifying antirheumatic drug (DMARD). The drug may be a nonsteriod anti-inflammatory drug (NSAID), which may be a propionic acid derivative, an acetic acid derivative, an enolic acid derivative, a fenamic acid derivative, or a selective Cox2 inhibitor. The drug may also be a corticosteroid or Methotrexate. The drug may be a biologic, which may be a TNF-α antagonist such as an anti-TNF-α antibody or a fusion protein that binds to TNF-α (Enbrel), an anti-CD20 mAb, an antagonist of costimulatory molecule CD80 and CD86 such as a monoclonal antibody or a fusion protein (CTLA4Ig) that binds to the two molecules, or an antagonist for a receptor of either IL-1 or IL-6. The CD24 and the other drug may be administrated together or sequentially.

b. Pharmaceutical Composition

The CD24 may be contained in a pharmaceutical composition, which may comprise a solvent, which may keep the CD24 stable over an extended period. The solvent may be PBS, which may keep the CD24 stable for at least 36 months at −20° C. (−15~−25° C.). The solvent may be capable of accommodating the CD24 in combination with the other drug.

c. Dosage

The dose to be used for human may ultimately be determined through a clinical trial to determine a dose with acceptable toxicity and clinical efficacy. The initial clinical dose for human may be estimated through pharmacokinetics and toxicity studies in rodents and non-human primates. The dose of CD24 may be 0.01 mg/kg to 1000 mg/Kg, and may be 1 to 500 mg/kg, depending on the severity of disease being treated and the route of administration.

d. Administration

The route of administration of the pharmaceutical composition may be parenteral. Parenteral administration includes, but is not limited to, intravenous, intraarterial, intraperitoneal, subcutaneous, intramuscular, intrathecal, intraarticular and direct injection into affected joints. For veterinary use, the agent may be administered as a suitably acceptable formulation in accordance with normal veterinary practice. The veterinarian can readily determine the dosing regimen and route of administration that is most appropriate for a particular animal. The pharmaceutical composition may be administered to a human patient, cat, dog, large animal, or an avian.

The CD24 may be administered simultaneously or metronomically with other treatments. The term "simultaneous" or "simultaneously" as used herein, means that the CD24 and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The CD24 may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. The CD24 may be administered at any point prior to a second treatment of the CD24 including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The CD24 may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The CD24 may be administered at any point prior after a previous CD24 treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The following examples are provided to illustrate the methods of the invention and are by no means to limit the use of the methods.

Example 1

Soluble CD24 Proteins

The extracellular domain of CD24 was fused to IgG1 Fc. The amino acid composition of the CD24 fusion protein is provided in FIG. 1. A replication-defective retroviral vector that drives expression of the CD24Ig fusion protein was then generated. The GPEx™ (an acronym for gene product expression) system offers several important advantages, the most important of which is the, on average, >1000 insertions/cell but with only 1 copy/insertion. Moreover, since the retrovirus preferentially inserts into the transcriptional active locus, the GPEx™ resulted in a high level of expression of the targeted protein. Stable cell lines that produce a high yield of CD24Ig were generated. In addition 45 grams of GLP grade products and ~100 grams of cGMP grade products were produced. The methods used for downstream processing of media harvested from the bioreactor are summarized in the flow chart below (FIG. 2).

Harvest Clarification

The bioreactor culture media was clarified using Cuno 60M02 Maximizer depth filters followed by a Millipore Opticap 0.22 um filter. The filtrate was collected into a sterile collection bag. Samples were obtained for CD24-Fc yield quantitation by ELISA.

Protein A Capture

The clarified media was passed over a column of Protein A resin (GE Healthcare MabSelect) at a concentration not exceeding 16 g/L of resin (based on ELISA) and a contact time of 4 minutes. The column was washed with the equilibration buffer (50 mM Tris+0.15M NaCl pH7.5), then with 10 mM sodium citrate/citric acid pH 6.0 for 5cvs. Bound CD24Ig was eluted from the column using 10 mM sodium citrate/citric acid pH 3.5

Viral Inactivation

The Protein A eluate fraction was immediately brought to pH 3.0 with the addition of 2M Hydrochloric acid and held at this pH for 30 minutes at ambient temperature. It was then brought to pH 5.0 with the addition of 1M Tris base, and filtered to clarity using a 0.65 um glass fiber filter (Sartorius Sartopure GF2) and 0.2 um (Sartorius Sartopore 2) into a sterile collection bag.

SP-Sepharose Chromatography

The viral inactivated material was applied to a column of SP-Sepharose (GE Healthcare) at a concentration not exceeding 25 g/L of resin (based on A280 nm of 1.22=1 mg/mL) and a linear flow rate of 250 cm/hr. The column was washed with the equilibration buffer (10 mM sodium citrate/citric acid pH 5.0) and bound CD24Ig was eluted from the column using 10 mM sodium citrate/citric acid+0.2M NaCl pH5.0. The effluent was collected into a sterile collection bag.

Mustang Q Chromatography

The SP-Sepharose elute was adjusted to pH 7.5 by the addition of 1M Tris base and diluted with WFI to reduce the conductivity. The diluted material was applied to a Mustang Q filter (Pall) at a concentration not exceeding 0.5 g/L of resin (based on A280 nm of 1.22=1 mg/mL) and at a flow rate of 5 column volumes/minute. The filter was washed with the equilibration buffer (10 mM Tris pH 7.5) and the CD24-Fc is contained in the flow through and is collected into a sterile collection bag.

Viral Filtration

The Mustang Q flow through was then filtered at a constant pressure of 30 psi through a 0.2 mM filter and a Millipore NFP viral filter (nominal pore size 20 nm) and was collected into a sterile collection bag.

Concentration and Final Formulation

The product was concentrated and diafiltered using a 10 kDa ultrafiltration membrane (Millipore Prep/Scale) into a 10 mM sodium phosphate, 150 mM sodium chloride pH 7.2 at approximately 10 mg/mL final concentration as determined by absorbance at 280 nm. Analytical samples were drawn from the bulk whilst in a biosafety cabinet. Labeling was performed and the samples were delivered to QC for testing while the bulk aliquots were stored at 2-8° C. pending release.

Viral Clearance Studies

The viral clearance validation was performed at Cardinal Health, NC, on samples prepared at CHM. Qualified scientists from Gala Biotech performed the chromatography and filtration steps in the Cardinal Health Viral Validation facility with the assistance of Cardinal Health personnel. The scale down procedure was developed from the 200 L scale process. Two viruses were chosen to be used in this study. The first was Xenotropic murine Leukemia virus (XMuLv), which is an enveloped RNA virus of 80-130 nm in size from the Retroviridae viral family. The second was Porcine Parvovirus (PPV), which is a nonenveloped DNA virus of 18-26 nm in size. This is considered a robust virus, and was expected to demonstrate a much lower viral reduction through the purification protocol than the XMuLv.

Example 2

CD24 Pharmacokinetics 1 mg of CD24IgG1 (CD24Fc) was injected into naïve C57BL/6 mice and collected blood samples at different timepoints (5 min, 1 hr, 4 hrs, 24 hrs, 48 hrs, 7 days, 14 days and 21 days) with 3 mice in each timepoint. The sera were diluted 1:100 and the levels of CD24Ig was detected using a sandwich ELISA using purified anti-human CD24 (3.3 μg/ml) as the capturing antibody and peroxidase conjugated goat anti-human IgG Fc (5 μg/ml) as the detecting antibodies. As shown in FIG. 4a. The decay curve of CD24Ig revealed a typical biphase decay of the protein. The first biodistribution phase had a half life of 12.4 hours. The second phase follows a model of first-order elimination from the central compartment. The half life for the second phase was 9.54 days, which is similar to that of antibodies in vivo. These data suggest that the fusion protein is very stable in the blood stream. In another study in which the fusion protein was injected subcutaneously, an almost identical half life of 9.52 days was observed (FIG. 4b). More importantly, while it took approximately 48 hours for the CD24Ig to reach peak levels in the blood, the total amount of the fusion protein in the blood, as measured by AUC, was substantially the same by either route of injection. Thus, from therapeutic point of view, different route of injection should not affect the therapeutic effect of the drug. This observation greatly simplified the experimental design for primate toxicity and clinical trials.

Example 3

CD24 for Treating RA

For decades, it has been assumed that RA is predominantly a T-cell mediated autoimmune diseases. In the last two decades, there is a reawaking on the possible role for antibodies and B lymphocytes in RA pathogenesis. Thus, in addition or rheumatoid factors, a host of autoreactive antibodies have been found in RA patients, although it has not been definitively addressed in human. However, several lines of evidence have demonstrated that in the mouse models, antibodies specific for either ubiquitous or tissue specific antigens are sufficient to cause RA symptoms. For instance, antibodies from the K/BxN TCR transgenic mice were found to be fully capable of transferring RA-like diseases in the new host. Likewise, a cocktail for 4 anti-collagen antibodies is now widely used to induce RA in the mouse. This model is now called CAIA, for collagen antibody-induced arthritis.

Genetic analyses of CAIA model indicate critical roles for complement. Although other possibilities exist, these requirements suggest potential involvement of antibody-mediated tissue damage in the pathogenesis of RA. The linkage between tissue damage and inflammation is a long-standing observation in immunology. Nearly two decades ago, Matzinger proposed what was popularly called danger theory. In essence, she argued that the immune system is turned on when it senses the dangers in the host. Although the nature of danger was not well defined at the time, it has been determined that necrosis is associated with the release of intracellular components such as HMGB1 and Heat-shock proteins, which were called DAMP, for danger-associated molecular patterns. DAMP were found to promote production of inflammatory cytokines and autoimmune diseases. In animal models, inhibitors of HMGB1 and HSP90 were found to ameliorate RA. The involvement of DAMP raised the prospect that negative regulation for host response to DAMP can be explored for RA therapy.

CD24-Siglec 10 Interaction in Host Response to Tissue Injuries

Figure 5A:
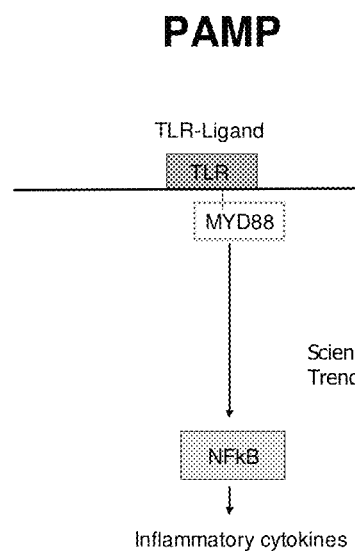
FIGS. 5A-B. CD24-Siglec G (10) interaction discriminates between PAMP and DAMP.
Figure 5B:
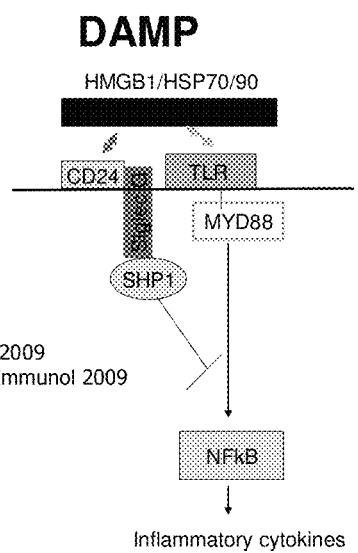

Using acetaminophen-induced liver necrosis and ensuring inflammation, we observed that through interaction Siglec G, CD24 provides a powerful negative regulation for host response to tissue injuries. CD24 is a GPI anchored molecules that is broadly expressed in hematopoietic cells and other tissue stem cells. Genetic analysis of a variety of autoimmune disease in human, including multiple sclerosis, systemic lupus erythromatosus, RA, and giant cell arthritis, showed significant association between CD24 polymorphism and risk of autoimmune diseases. Siglec G is a member of I-lectin family, defined by their ability to recognize sialic acid containing structure. Siglec G recognized sialic acid containing structure on CD24 and negatively regulates production of inflammatory cytokines by dendritic cells. In terms of its ability to interact with CD24, human Siglec 10 and mouse Siglec G are functionally equivalent. However, it is unclear if there is a one-to-one correlation between mouse and human homologues. Although the mechanism remains to be full elucidated, it is plausible that SiglecG-associated SHP1 may be involved in the negative regulation. These data, reported in Science recently, leads to a new model in which CD24-Siglec G/10 interaction may play a critical in discrimination pathogen-associated molecular pattern (PAMP) from DAMP (FIG. 5).

At least two overlapping mechanisms may explain the function of CD24. First, by binding to a variety of DAMP, CD24 may trap the inflammatory stimuli to prevent their interaction with TLR or RAGE. This notion is supported by observations that CD24 is associated with several DAMP molecules, including HSP70, 90, HMGB1 and nucleolin. Second, perhaps after associated with DAMP, CD24 may stimulate signaling by Siglec G. Both mechanisms may act in concert as mice with targeted mutation of either gene mounted much stronger inflammatory response. In fact, DC cultured from bone marrow from either CD24−/− or Siglec G−/− mice produced much higher inflammatory cytokines when stimulated with either HMGB1, HSP70, or HSP90. In contrast, no effect were found in their response to PAMP, such as LPS and PolyL:C. These data not only provided a mechanism for the innate immune system to distinguish pathogen from tissue injury, but also suggest that CD24 and Siglec G as potential therapeutic targets for diseases associated with tissue injuries.

Therapeutic Effect of CD24Fc on Collagen-Antibody-Induced Arthritis

Given the suspected role for innate immunity to tissue injury in the pathogenesis of RA and the role for CD24-Siglec G/10 pathway in negatively regulate such response, the possibility of stimulating this pathway to treat RA was explored. Pathogenesis of essentially all autoimmune diseases involves induction of immune response to autoantigen and autoimmune destruction. The autoimmune destructive phase was focused on, based the novel function of CD24-Siglec G interaction. Therefore, for the preliminary analysis, collagen antibody-induced arthritis model was adopted to evaluate potential therapeutic effect.

Figure 6A:
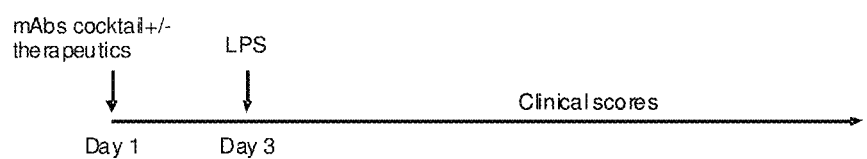
FIGS. 6A-B. A single injection of CD24Fc reduces clinical score of CAIA.
Figure 6B:
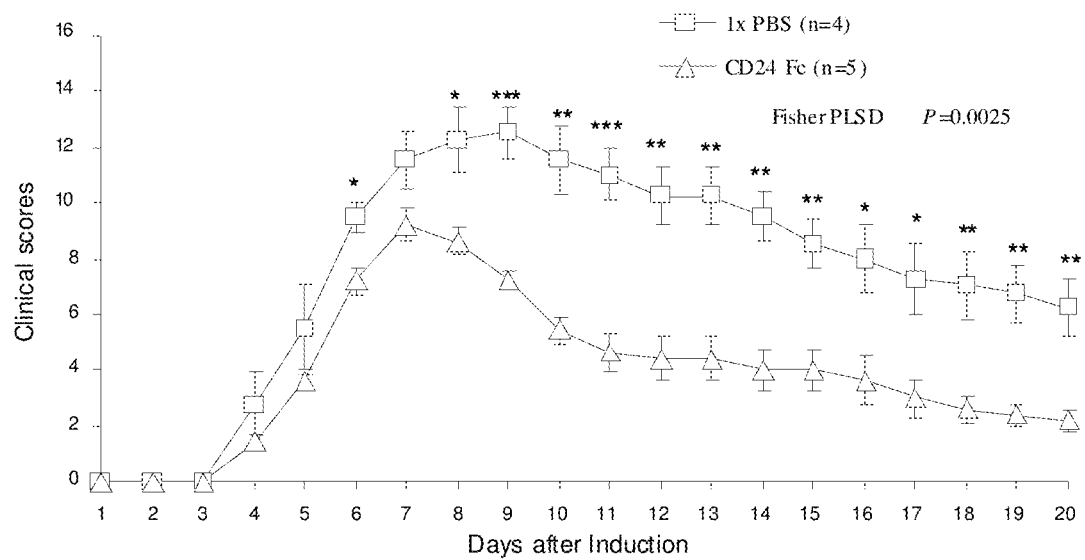

As shown in FIG. 6a, the CAIA was induced on 8 weeks old BALB/c mice by i.v. injection of a cocktail of 4 anti-collagen mAbs (MD Biosciences, St. Paul, Minn.) at 2 mg/mouse on day 1, and i.p. injection of 100 μg/mouse of LPS (MD Bioscience) on day 3. The mice were treated on day 1 with either 1 mg CD24Fc or equal volume of 1×PBS vehicle as negative control. As shown in FIG. 6b, in comparison with vehicle control, CD24Fc provided highly significant therapeutic effects.

Figure 7A:
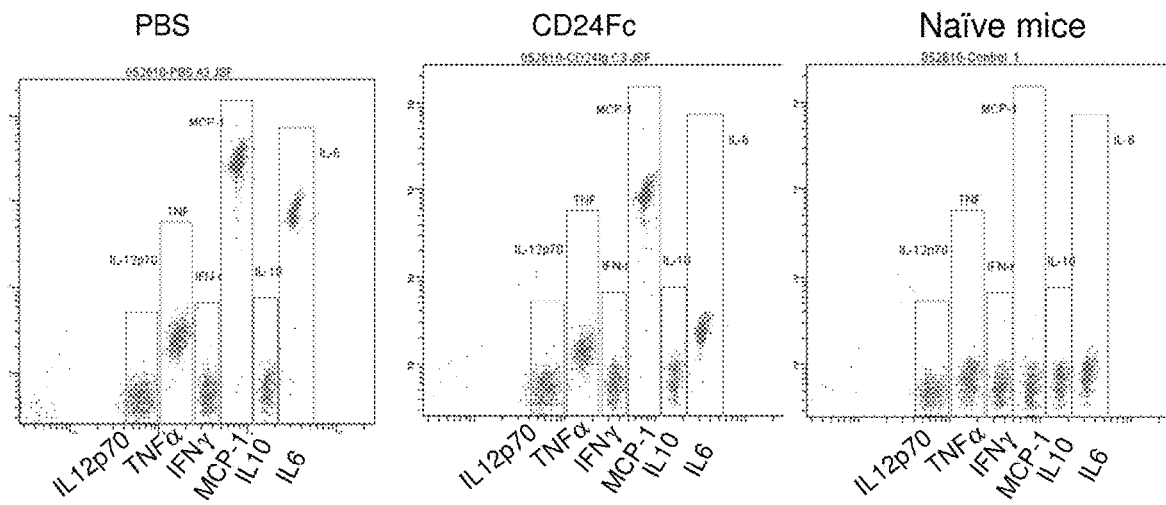
FIGS. 7A-B. CD24Fc reduces the levels of inflammatory cytokines in the joint and CAIA. CAIA initiated and treated as diagramed in FIG. 6A. The inflammatory cytokines were measured by cytokine bead array from BD Pharmingen.
Figure 7B:
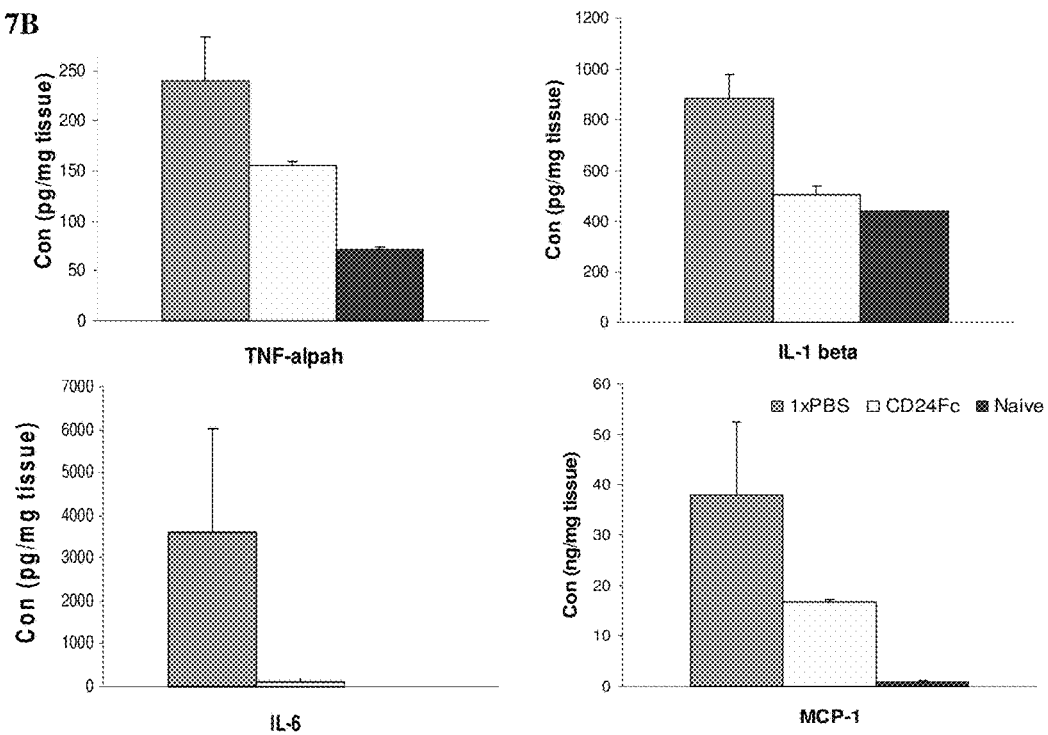

To understand the mechanism by which CD24Fc reduces arthritis in this model, cytokines were measured from homogenized joints of CD24Fc treated mice or PBS control group, and measured the supernatant of 200 μg tissue homogenates by cytokine beads array. A typical example is shown in FIG. 8a, while the summary data are shown in FIG. 7b. These data demonstrated that systematically administrated CD24 reduces the levels of multiple inflammatory cytokines including TNF-α, IL-6, MCP-1(CCL2) and IL-1β.

Figure 8:
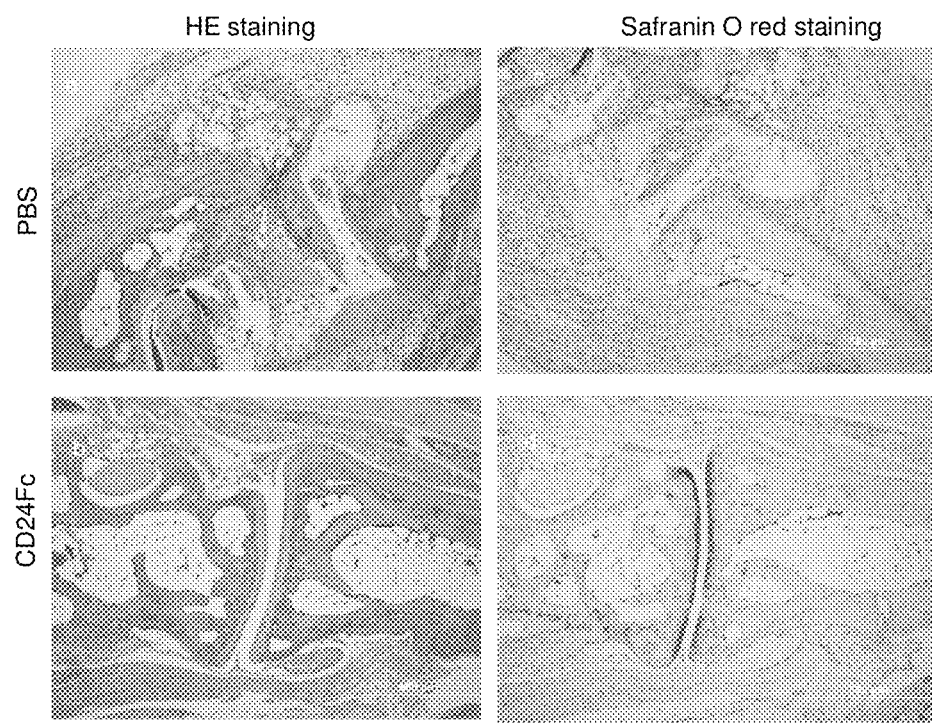
FIG. 8. CD24Fc reduces inflammation and destruction of cartilage in the joint. On day 7, front and hind paws were dissected from both CD24Fc treated and control mice, fixed in 4% paraformaldehyde for 24 hours followed by decalcification with 5% formic acid. The paws were then embedded in paraffin and the longitudinal section were stained with H&E and Safranin O red (Sigma-Aldrich).

The effect of CD24Fc is substantiated by histological analysis of the synovial joints of CAIA mice, as presented in FIG. 8. On day 7 after induction of arthritis, H&E staining demonstrated that the joint synoviums in the PBS group are heavily infiltrated with inflammatory cells including neutrophil, macrophage, and lymphocytes (FIG. 8a). This was much reduced in the CD24Fc treated mice (FIG. 8b). In addition, sever cartilage damages were revealed by the loss of safranin O red staining in PBS-treated (FIG. 8c) mice, but not CD24Fc-treated group (FIG. 8d).

Figure 9:
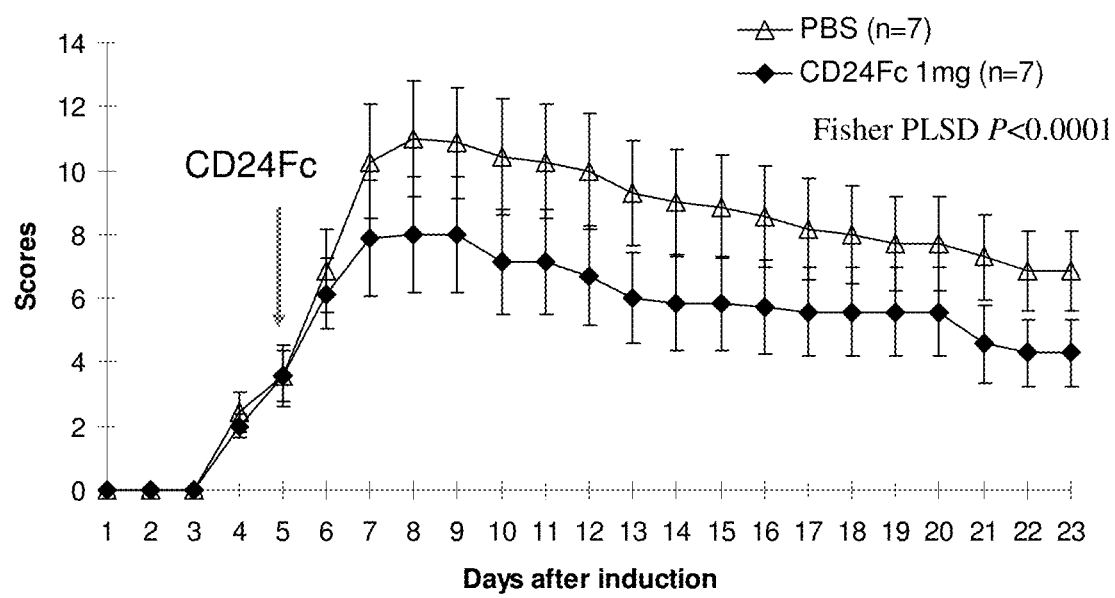
FIG. 9. Therapeutic effect of CD24Fc administrated on day 5 of CAIA induction. The CAIA-induced mice were randomized into two groups, receiving either vehicle (PBS) or CD24 Fc. The mice were scored double blind. Representative of three independent experiments are shown.

To determine whether mice, CD24Fc have therapeutic effect on ongoing RA, treatment was started at either 5 or 7 days after induction of RA. As shown in FIG. 9, significant reduction of RA score was observed as soon as two days after CD24Fc treatment. The therapeutic effect lasted for the remaining period of observation even without additional treatment. These data further strengthen the therapeutic potential of CD24Fc on ongoing diseases.

Figure 10A:
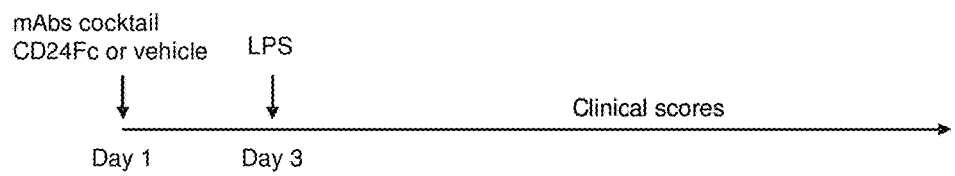
FIGS. 10A-B. Low doses of CD24Fc prevent development of CAIA.
Figure 10B:
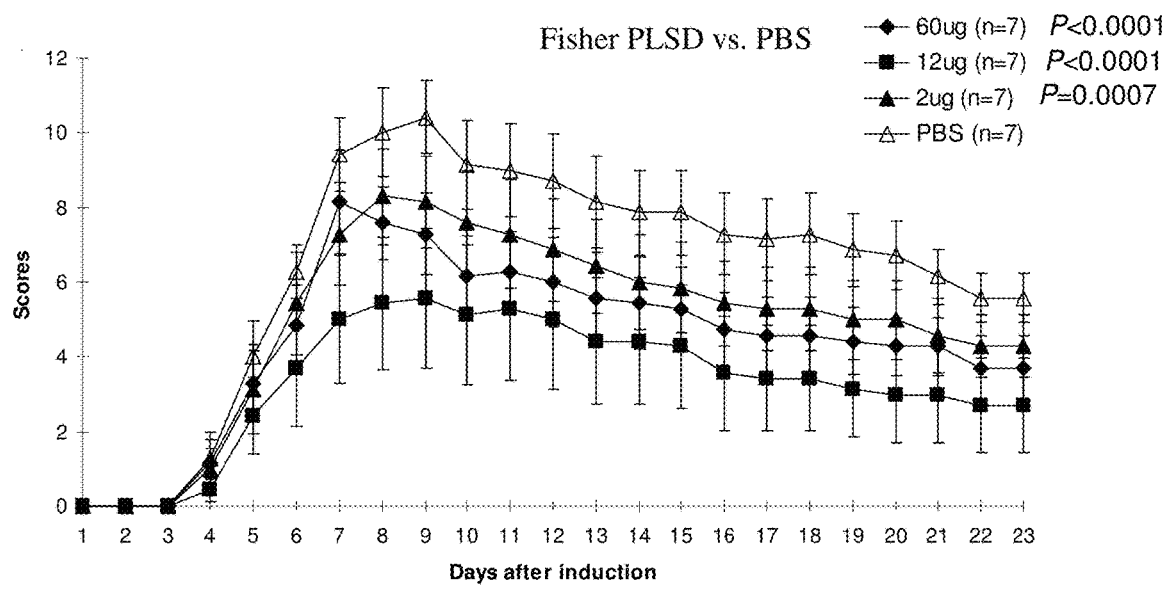

In order to estimate the therapeutic doses of CD24Fc in human, CD24Fc was titrated through a wide range of doses. As shown in FIG. 10, as little as 2 microgram/mice is sufficient to have statistically significant therapeutic effect.

Siglecg-Dependent Therapeutic Effect of CD24Fc

Figure 11A:
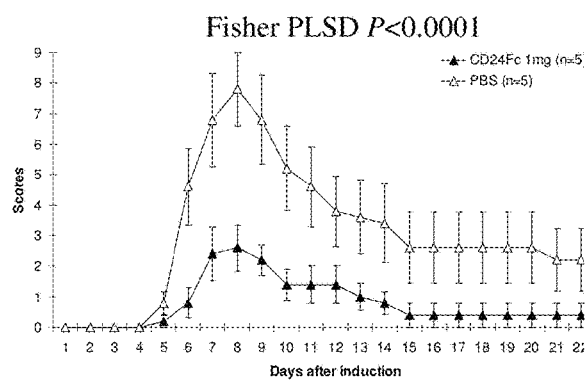
FIGS. 11A-B. Siglecg is essential for therapeutic effect of CD24Fc, WT (FIG. 11A) and Siglecg$^{-/-}$ mice (FIG. 11B) received either vehicle control or CD24Fc in conjunction of a cocktail of anti-collagen mAbs. The clinical scores were recorded daily double blind.
Figure 11B:
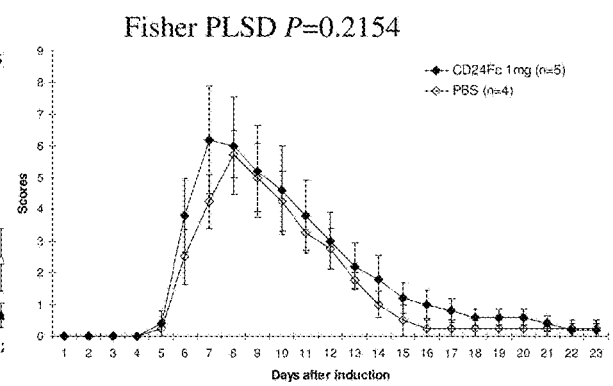

To determine whether CD24Fc protect mice by interacting with Siglec G, we determined if the therapeutic effect depends on the Siglecg gene. Since the Siglecg-deficient mice were produced with ES cells from C57BL/6 mice, we used WT C57BL/6 mice as control. As shown in FIG. 11a, since the B6 mice are known to be less susceptible to the CAIA, the overall disease score is lower than that observed in the BALB/c mice. Nevertheless, a single injection of the CD24Fc essentially wiped out the clinical signs in the WT mice. Importantly, even though the disease is less severe in the Siglecg-deficient mice, CD24Fc had no therapeutic effect. Therefore, the therapeutic effect of CD24Fc is strictly dependent on the Siglecg gene.

Taken together, the data described herein demonstrates high therapeutic efficacy of CD24Fc for CAIA. Given our extensive data on safety, stability and our successful manufacture of CD24Fc all point to great potential of the fusion protein as a therapeutic for RA.

Example 4

Toxicity and Pharmacokinetics of CD24

Toxicity

A study of CD24Fc in mice was performed in order to evaluate the toxicity and systemic exposure of CD24Fc when intravenously administered to mice once weekly for four weeks, and the reversibility of toxicity following a four-week recovery period. A total of 320 male and female mice were assigned to Groups 1-4 for evaluation of the toxicity (20/sex/group) and reversibility (20/sex/group). All of these mice were treated intravenously with either PBS buffer or CD24Fc at doses of 12.5, 35, or 125 mg/kg once weekly for 4 weeks. A total of 360 mice were assigned to Groups 5-8 for evaluation of the systemic exposure of CD24Fc following the first dose (3/sex in Group 5 and 27/sex/group in Groups 6-8) and the last dose (6/sex in Group 5 and 30/sex/group in Groups 6-8). All of these mice were treated intravenously with either PBS buffer or CD24Fc at doses of 12.5, 35, or 125 mg/kg once on Day 1 or once weekly for 4 weeks.

No morbidity or mortality was found in mice treated with either PBS buffer or CD24Fc, with the exception that one male mouse treated with 35 mg/kg of CD24Fc in Group 7 was found dead on Day 21. This death occurred in 1/680 of mice and did not appear to be associated with the treatment. No treatment-related changes were noted in clinical observations, body weights, food consumption, ophthalmology, hematology, coagulation, clinical chemistry, organ weights, and organ-to-body or to-brain weight ratios. No treatment-related macroscopic and microscopic findings were observed in all examined animals.

Anti-CD24Fc antibody was detected in 10/30 of mice on Day 30 and 12/30 of mice on Day 57, which appeared to be dose dependent with no difference between male and female mice. A higher systemic exposure following the first dose and last dose was observed in male animals compared to female animals. An approximately linear increase in AUC values was observed when mice were treated with increasing doses of CD24Fc from 12.5 mg/kg to 125 mg/kg. An accumulation of CD24Fc in mice was observed after dosing once weekly for four weeks.

In summary, no observed adverse effects were noted in mice treated with CD24Fc at doses of 12.5, 35 or 125 mg/kg once weekly for 4 weeks with a 4 week recovery period. The NOAEL was considered to be equal to or greater than 125 mg/kg.

Another study of CD24Fc was performed in cynomolgus monkeys to examine the pharmacokinetics and potential toxicity, acquired immunity, and immunogenicity following administration of CD24Fc administered by intravenous infusion once weekly for four weeks, and to evaluate recovery from any effects of the test article over a dose-free period of at least 10 weeks. The test article, CD24Fc (Lot No. FP004.12-06097-001), and the control article, 1× phosphate-buffered saline (PBS), pH 7.2 (Lot No. 654446), were supplied as a clear, colorless, preformulated aqueous solution and as a preformulated aqueous solution, respectively. The test article formulation was used as received for dose administration.

Forty experimentally naive cynomolgus monkeys (20 males and 20 females), 2.9 to 4.7 years of age for the males and 2.9 to 5.0 years of age for the females, and weighing 2.1 to 3.2 kg for the males and 2.2 to 2.9 kg for the females at the outset (Day −1) of the study, were assigned to dose groups as shown in Table 2 below.

All animals were dosed via 1-hour intravenous infusion once weekly for 4 consecutive weeks. The first day of dosing was designated Day 1 (04 and 5 Sep. 2009, Sets A and B, respectively). The animals were evaluated for changes in clinical signs (evaluations of morbidity and/or mortality [twice daily] and cage side observations [once daily], body weight (Weeks −2 and −1, and weekly thereafter), electrocardiography (prestudy and Day 28), ophthalmology (prestudy and Day 28), and clinical pathology indices (including serum chemistry, hematology, and coagulation (three prestudy and Days 28 and 98), and urinalysis [via cystocentesis on Days 28 and 98]). Blood samples were collected for toxicokinetic analysis predose, 15 minutes, and 6, 24, and 72 hours in relation to dose administration on Days 1 and 22, predose on Day 8, and on Day 29 (at the same time of day as Day 22 end of infusion). Blood samples for flow cytometry were collected prestudy (three time points), and on Days 28 and 98. Blood samples for anti-drug antibodies (ADA) were collected prestudy and on Days 28 and 98. To evaluate the T-cell dependent antibody response (TDAR), the animals were immunized with a 1:1 emulsion of keyhole limpet hemocyanin (KLH) and Incomplete Freund's Adjuvant (IFA) injected intramuscularly on the thigh to achieve a dose of 750 mg/animal on Day 10, and to recovery animals on Day 84. Blood samples for anti-KLH response were collected prestudy, and on Days 20, 24, 28, 94, and 98. Twenty four (24) animals (3/sex/group) were euthanized one week after the last dose. The remaining 16 animals (2/sex/group) were continued on the study without further dosing, and euthanized on Day 98 (76 days after the last dose). At termination, a full necropsy was conducted on all animals, and tissues were collected, preserved, processed, and examined microscopically by a Study Pathologist certified by the American College of Veterinary Pathologists (ACVP). At recovery, a full necropsy was conducted on all animals, and tissues were collected, preserved, processed, and selected tissues (based on clinical pathology and gross observations) were examined microscopically by a study pathologist certified by the ACVP.

The results showed that CD24Fc administered via 1-hour intravenous infusion once weekly for 4 consecutive weeks at 12.5 mg/kg/week (Group 2), 35 mg/kg/week (Group 3), or 125 mg/kg/week (Group 4) was generally well tolerated in male and female cynomolgus monkeys through a 4-week dosing period, followed by a 10 week recovery period. There were no CD24Fc-related changes in clinical observations, food consumption, body weights, electrocardiographic measurements, ophthalmic examinations, serum chemistry (one exception noted below), coagulation, urinalysis parameters, macroscopic findings, or organ weights or organ weight ratios. There were no CD24Fc-related changes in peripheral blood mononuclear cell subset counts obtained by flow cytometry, or anti-KLH immunoglobulin G (IgG) responses to KLH challenge. There was a possible approximately 2-fold increase in ALP related to CD24Fc for one male administered 35 mg/kg/week at Day 98 compared to predose and Day 28 values. There was also a possible CD24Fc-related slight decrease in hemoglobin at Day 28 for 35 mg/kg/week males. The magnitude and/or nature of these changes was not considered adverse in this study. On Day 28, one male administered 35 mg/kg/week had an approximate 13% decrease in hemoglobin concentration. On Day 98 (76 days after the last dose), changes in hematology for this animal included a 21% decrease in hemoglobin, a 16% increase in red blood cell counts, a 21% decrease in mean cell volume (MCV), a 32% decrease in mean cell hemoglobin (MCH), a 14% decrease in mean cell hemoglobin concentration (MCHC), a 24% increase in red cell distribution width (RDW), and an approximately 2-fold increase in platelet and reticulocyte counts compared to prestudy (Day −2) levels. Day 98 blood smear analysis documented hypochromic red blood cells, microcytosis, anisocytosis, schistocytes, poikilocytes, and spherocytes, as well as an apparent increase in platelet numbers. These hematology changes are not considered typical findings in cynomolgus monkeys. However, no corresponding histopathology abnormalities were identified, and these hematology findings were not observed in any other animals in the mid-dose (35 mg/kg/week) or high-dose (125 mg/kg/week) groups.

At Day 29 terminal necropsy, there were microscopic findings of fibrin thrombi in hepatic sinusoids and multifocal glial nodules in the brain of one female administered 125 mg/kg/week. The changes were mild and occurred only in one animal, but they were not typical background findings. More extensive independent studies established that the lesion was also observed in placebo samples and therefore was not drug-related. At recovery necropsy, histopathologic analysis of the following subset of tissues was performed based on clinical pathology or gross findings: all tissues except for mammary glands from a male administered 35 mg/kg/week, the duodenum from another male administered 35 mg/kg/week, and testes from one male administered 125 mg/kg/week. No microscopic findings were found related to the administration of CD24Fc.

CD24Fc was detected in serum samples from all dosed animals. No measurable amount of CD24Fc was detected in control or predose serum samples. Incurred sample reanalysis (ISR) was performed, and the results met the acceptance criteria. Serum was screened for the presence of anti-CD24Fc antibody. Seven animals out of the 40 total were identified as positive at the prestudy time point (17.5%). This rate of positive samples prior to test article administration is similar to the rate observed in the validation (12.5%) which demonstrated a subpopulation of animals with pre-existing anti-CD24Fc antibodies. Three animals were identified as positive during the dosing period of the study. The validation experiment also demonstrated that 10 μg/mL of CD24Fc inhibited the measurement of anti-CD24Fc antibodies in reference to the positive control, and all dose groups at the Day 29 toxicokinetic time point had concentrations greater than 10 μg/mL measured in serum. Only one animal (125 mg/kg/week dose group) screened positive for anti-CD24Fc antibodies within the recovery interval.

Based on the hematology findings, the no-observed-adverse-effect level (NOAEL) for CD24Fc was considered to be 12.5 mg/kg/week under the conditions of this study when administered once weekly for four weeks.

Pharmacokinetics of CD24 in Mice and Monkeys

The pharmacokinetics of CD24Fc were examined in the mouse and cynomolgus monkeys. These animal PK studies were carried out by two preclinical contract research organizations. The mouse study was performed by JOINN Laboratory at Beijing, China, while the cynomolgus monkey study was carried out by Charles River Laboratory at Reno, Nev., USA. Both studies were in compliance with the Good Laboratory Protocol (GLP) and the final reports were audited. As an independent report, the WinNonLin analysis of pharmacokinetic characterizations of CD24Fc in this report were performed by either JOINN Laboratory at Beijing, China (PK in mouse) or Oncolmmune Inc. (PK in cynomolgus monkey).

In the mouse PK study, CD24Fc was intravenously administered to mice once weekly for four weeks. A total of 360 mice were assigned to Groups 1-4 for evaluation of the systemic exposure of CD24Fc following the first dose (3/sex in Group 1 and 27/sex/group in Groups 2-4) and the last dose (6/sex in Group 1 and 30/sex/group in Groups 2-4). All of these mice were treated intravenously with either PBS buffer or CD24Fc at doses of 12.5, 35, or 125 mg/kg once weekly for 4 weeks. Blood samples were collected at each time point from 3 mice/sex/group in Groups 1-4 via orbital vein for determination of the serum concentrations of CD24Fc. For Group 1, blood samples were collected prior to dosing on Days 1 and 29 and at 4 hours after dosing on Day 29. For Groups 2-4, blood samples were collected at 5 and 15 minutes; and 1, 4, 8, 24, 48, 72, and 168 hours following dosing on Days 1 and 29; and 366 hours following dosing on Day 29.

Figure 17A:
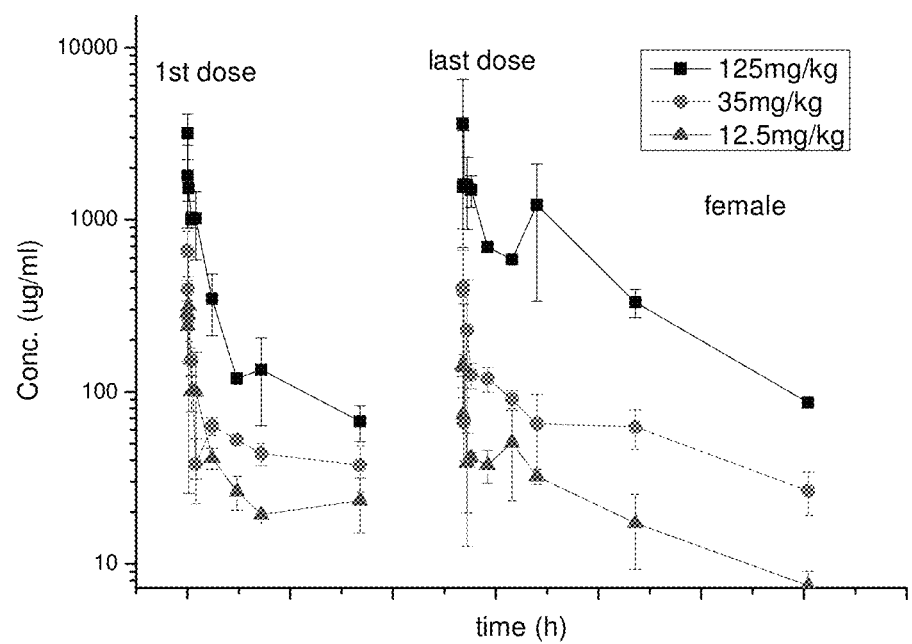
FIGS. 17A-B.
Figure 17B:
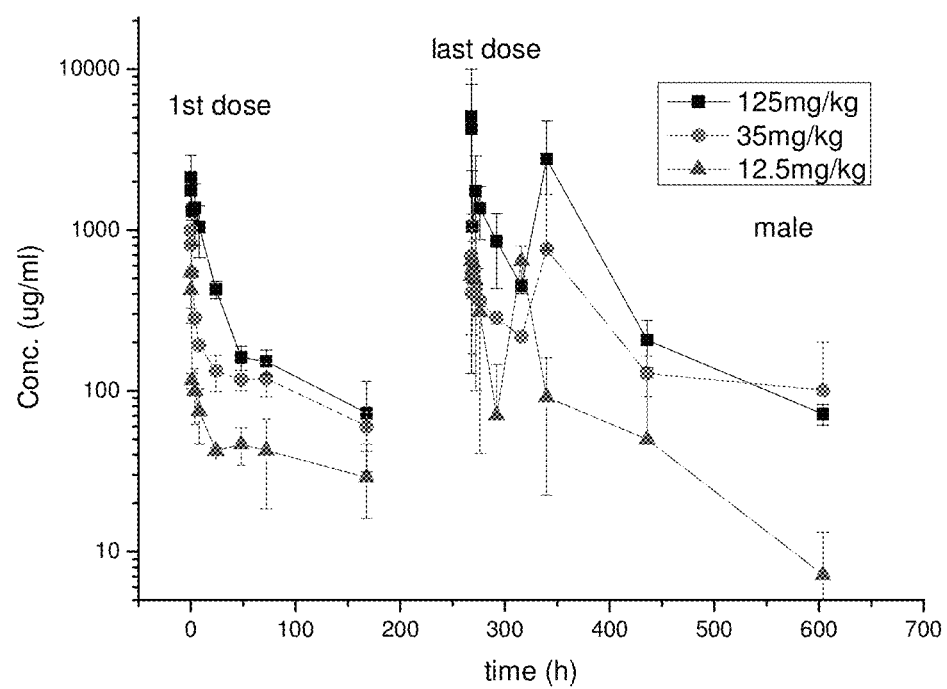

The summarized results of the mouse serum concentration of CD24Fc following the first dose and last dose are included in Table 1, and the WinNonlin analysis of serum CD24Fc concentration vs. time points is included in FIG. 17.

TABLE 1

Pharmacokinetic parameters of CD24Fc in mice

| | unit | Female | | | Male | | |
|---|---|---|---|---|---|---|---|
| | | 125 mg/kg | 35 mg/kg | 12.5 mg/kg | 125 mg/kg | 35 mg/kg | 12.5 mg/kg |
| First dose parameters | | | | | | | |
| $T_{1/2}$ | h | 46.36 | 59.18 | 63.93 | 48.51 | 70.57 | 63.00 |
| $C_{max}$ | mg/ml | 3.17 | 0.66 | 0.32 | 2.13 | 0.99 | 0.54 |
| $AUC_{(0-168\ h)}$ | h * mg/ml | 39.04 | 8.65 | 5.85 | 44.00 | 19.99 | 7.55 |
| $AUC_{inf}$ | h * mg/ml | 43.53 | 11.84 | 8.00 | 49.10 | 26.13 | 10.18 |
| Vd | ml/kg | 192.06 | 252.33 | 144.09 | 178.18 | 136.39 | 111.55 |
| Cl | ml/h/kg | 2.87 | 2.96 | 1.56 | 2.55 | 1.34 | 1.23 |
| MRT | h | 39.08 | 67.85 | 56.68 | 39.58 | 61.09 | 66.21 |
| $C_{max}$ ratio | | 10.04 | 2.09 | 1.00 | 3.92 | 1.83 | 1.00 |
| AUC ratio | | 5.44 | 1.48 | 1.00 | 4.82 | 2.57 | 1.00 |
| Last dose parameters | | | | | | | |
| $t_{1/2}$ | h | 87.51 | 131.86 | 128.63 | 75.02 | 167.27 | 58.90 |
| $C_{max}$ | mg/ml | 3.61 | 0.40 | 0.14 | 5.07 | 0.76 | 0.65 |
| $AUC_{(0-336\ h)}$ | h * mg/ml | 177.00 | 21.35 | 7.68 | 251.18 | 88.20 | 35.75 |
| $AUC_{inf}$ | h * mg/ml | 187.95 | 26.41 | 9.07 | 258.93 | 112.49 | 36.36 |
| Vd | ml/kg | 83.96 | 252.16 | 255.74 | 52.25 | 75.08 | 29.22 |
| Cl | ml/h/kg | 0.67 | 1.33 | 1.38 | 0.48 | 0.31 | 0.34 |
| MRT | h | 91.64 | 121.30 | 106.00 | 77.98 | 106.29 | 70.30 |
| $C_{max}$ ratio | | 25.09 | 2.81 | 1.00 | 7.86 | 1.17 | 1.00 |
| AUC ratio | | 20.72 | 2.91 | 1.00 | 7.12 | 3.09 | 1.00 |
| Faccu | | 4.32 | 2.23 | 1.13 | 5.27 | 4.31 | 3.57 |

Figure 18A:
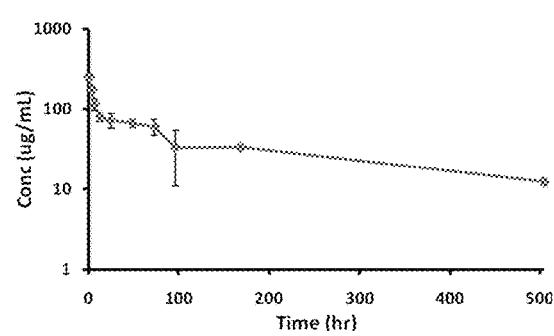
FIGS. 18A and B show CD24Fc serum concentrations vs. time in cynomolgus monkeys (12.5 mg/kg dose).
Figure 18B:
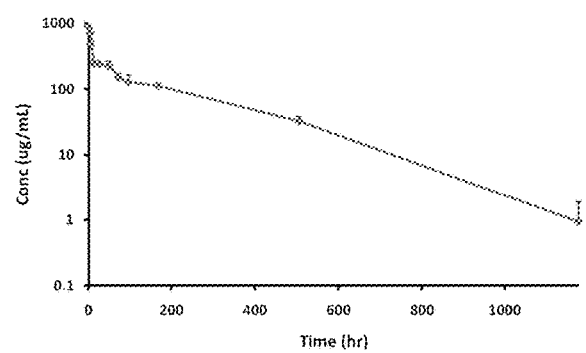

The summarized results of the monkey serum concentrations of CD24Fc following the single dose are included in Table 2, and the WinNonlin analysis of serum CD24Fc concentration vs. time points is included in FIG. 18.

TABLE 2

Pharmacokinetic parameters of CD24Fc in cynomolgus monkeys

| PK Parameters | unit | 35 mg/kg | 12.5 mg/kg |
|---|---|---|---|
| $t^{1/2}$ | h | 148.39 | 188.29 |
| Cmax | mg/ml | 0.89 | 0.25 |
| AUC(0-t) | h * mg/ml | 67.09 | 17.02 |
| AUCinf | h * mg/ml | 67.31 | 20.06 |
| Vd | ml/kg | 108.21 | 153.10 |
| Cl | ml/h/kg | 0.52 | 0.62 |
| MRT | h | 204.22 | 151.07 |
| Cmax ratio | | 3.56 | 1.00 |
| AUC ratio | | 3.36 | 1.00 |

Example 5

A Variant CD24 has Improved Activity Over Wild-Type CD24

This example shows that a CD24 polypeptide containing human CD24 missing the polymorphic amino acid at position 57 (SEQ ID NO: 1) (CD24Fc) is more effective for treating RA than a CD24 polypeptide containing wild-type CD24 (SEQ ID NO: 2) (CD24$^V$Fc).

Methods

Antibodies, Fusion Proteins and Other Materials

CD24Fc and CD24vFc were manufactured by Oncolmmune, Inc.; Bovine type II collagen, Catalog No. 20022, Chondrex Inc., Redmond, Wash.; a cocktail of 4 anti-collagen mAbs Catolog No. CIA-MAB-50 for BALB/c and CIA-MAB-2C for C57BL/6 mice, MD Bioproducts, St. Paul, Minn.; Chick type II collagen, Catalog No. 20011, Chondrex Inc., Redmond, Wash.; Complete Freund's adjuvant: Catalog No. 7008, Chondrex Inc., Redmond, Wash., with heat-killed *M. tuberculosis* H37 Ra (non-viable) at concentration of 1 mg/ml; Complete Freund's adjuvant: Catalog No. 7023, Chondrex Inc., Redmond, Wash., with heat-killed *M. tuberculosis* H37 Ra (non-viable) at concentration of 5 mg/ml; Incomplete Freund's adjuvant: Catalog No. 7002, Chondrex Inc., Redmond, Wash.; Lipopolysaccharide (LPS), Catalog No. 9028, Chondrex Inc., Redmond, Wash., from *E. coli* 0111:B4; Cytometric Bead Array (CBA) Mouse Inflammation Kit, Catalog No. 552364, BD Biosciences, San Jose, Calif.; Cytometric Bead Array (CBA) Human Inflammatory Cytokines Kit, Catalog No. 551811, BD Biosciences, San Jose, Calif.

Experimental Animals

BALB/cAnNCr (01B05, NCI) and C57BL/6NCr (01055, NCI) mice, male, 7 weeks old, were purchased from the National Cancer Institute (NCI) at Frederick, Md. DBA/1J (000670, JAX) mice, male, 7 weeks old, were received from Jackson Laboratories. All mice were quarantined for 7 days prior to immunization. During quarantine, the animals were examined for general health and acceptability for use in this study. Individual animals were identified by ear mark. Animal cages were identified by study number, animal number, and group number. To minimize cage variation, different treatments were given to individual mouse in the same cages and scored in a double-blind protocol.

CAIA Model

BALB/c mice (8 weeks old) received mAbs (2 mg/mouse) on day 1 in conjunction with either vehicle or fusion proteins. Mice received LPS (100 μg/mouse) on day 3, and were observed daily for 3 weeks. The fusion proteins (0.2 or 1 mg/mouse) or vehicles were injected once on day 1. In the C57BL/6 mice, the dose of anti-collagen antibodies was either 2 mg/mouse or 4 mg/mouse.

CIA Models

CIA in DBA/1 mice. On day 1, 8-week old DBA/1 mice were immunized with 100 μL of collagen-CFA emulsion (made by mixing 2 mg/ml of bovine type II collagen with equal volume of CFA containing 1 mg/ml of *M. tuberculosis*) subcutaneously at the base of the tail. On day 10, mice were booster-immunized with 60 μL of collagen-IFA emulsion (made by mixing 2 mg/ml of collagen with equal volume of IFA) subcutaneously 1.5 cm from the tail base. Treatments were initiated either before or after the development of symptom of arthritis.

CIA in C57BL/6 mice. On day 1, 8-week old C57BL/6 mice were immunized with 100 μL of collagen-CFA emulsion (made by mixing 4 mg/ml of chick type II collagen with equal volume of CFA containing 5 mg/ml of *M. tuberculosis*) intradermally at the base of the tail. On day 21, booster immunization with the same collagen-CFA emulsion was administered intradermally 1.5 cm from the tail base. On day 28, mice with clinical symptoms were randomized to receive either vehicle or CD24Fc.

Treatment in RA Models

The scoring of arthritis was based on the following scale. 0, normal; 1, mild, but definite redness and swelling of the ankle or wrist, or apparent redness and swelling limited to individual digits, regardless of the number of affected digits; 2, moderate redness and swelling of ankle of wrist; 3, severe redness and swelling of the entire paw including digits; 4, maximally inflamed limb with involvement of multiple joints. A combined score of 4 limbs in a mouse was reported as the disease score for the mouse.

Prophylactic treatment in CAIA was initiated at the same time as the anti-collagen antibodies.

Prophylactic model in CIA model in DBA/1 mice: On day 17, the immunized mice were randomly divided into two groups and were treated with vehicle (PBS) or given doses of CD24Fc. The mice were observed double blind for three weeks.

Therapeutic CIA in DBA/1 model with ongoing diseases were initiated at either 25 days after the first immunization using mice with clinical scores from 3 to 8.

Therapeutic CIA in the C57BL/6 mice was initiated on day 28 or using only those mice with a clinical score from 3 to 8.

Statistical Methods

Group means and standard deviation values (when deemed appropriate) were calculated for all numerical data obtained. The difference between CD24Fc and control mice was statistically analyzed with Fisher PLSD Test, or t-test for pairwise comparisons.

Results

Figure 12A:
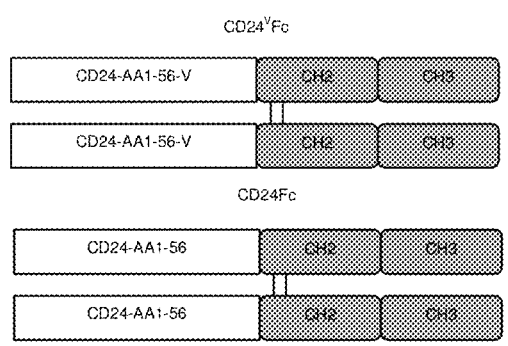
FIGS. 12A-F. Construction of CD24'Fc and CD24Fc.
Figure 12C:
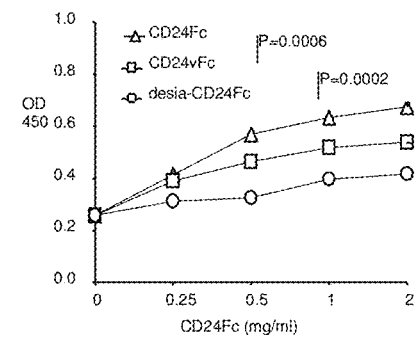
Figure 12B:
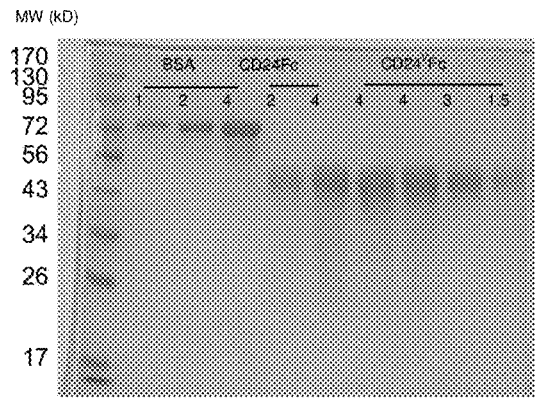

Therapeutic Effect of Non-Polymorphic CD24Fc on Collage-Antibody-Induced Arthritis Human mature CD24 exists in two allelic forms, in which either a valine or alanine is present at the C-terminus (position 57 of the CD24 amino acid sequence). Fusion proteins including either allelic form may provoke anti-drug antibodies in some RA patients. Thus, in order to avoid immunogenicity, it was tested whether the polymorphic residue can be removed from CD24, while maintaining regulatory function of CD24. As diagrammed in FIG. 12A, two fusion proteins were created, one with the entire extracellular domain of $CD24^V$ allele ($CD24^V$Fc) (the mature CD24 sequence having SEQ ID NO: 2), while the other had a one amino acid deletion at the C-terminus of the resulting mature CD24 (CD24Fc) (the mature CD24 sequence having SEQ ID NO: 1). Both forms were expressed and purified to a similar degree (FIG. 12B).

Figure 12D:
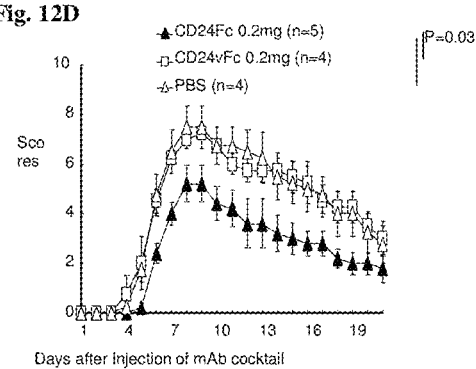
Figure 12E:
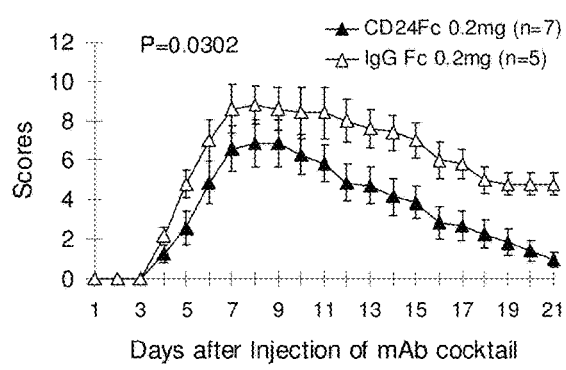
Figure 12F:
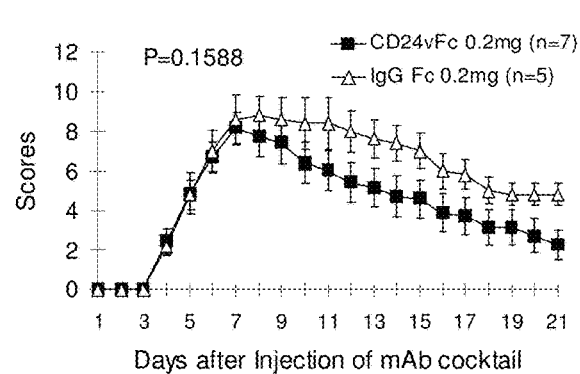

To determine whether the valine on CD24 is required for CD24-Siglec 10 interaction, their binding of CD24Fc and $CD24^V$Fc to a Siglec 10Fc fusion protein was compared. As shown in FIG. 12C, CD24Fc interacted with Siglec 10Fc in a dose-dependent manner. The interaction depended on sialic acid on CD24Fc as pre-treatment of CD24Fc with sialidase prevented the binding. Surprisingly, while $CD24^V$Fc also interacted with Siglec 10Fc, the interaction was significantly weaker than that of CD24-Fc-Siglec 10Fc. The CAIA was induced in 8 week-old BALB/c mice by i.v. injection of a cocktail of 4 anti-collagen mAbs in conjunction with $CD24^V$Fc, CD24Fc, human IgG1Fc or equal volume of 1×PBS vehicle as negative control. As shown in FIG. 12D, in comparison with vehicle control, CD24Fc provided highly significant therapeutic effects. Surprisingly, $CD24^V$Fc was far less effective, with activity not very different from the negative control. In experiments similar to the ones shown in FIG. 12D, FIGS. 12E and 12F also show that CD24Fc is more effective than $CD24^V$Fc, although unlike in the experiments in FIG. 12D, $CD24^V$Fc did have more activity than the negative control. Comparisons of the therapeutic effects of CD24Fc and $CD24^V$FC indicate that deleting the polymorphic amino acid residue is not only likely to remove a potential issue of immunogenicity, but it also significantly increases the anti-inflammatory activity of the CD24 protein. Since the Fc portion was identical in the two constructs, the therapeutic effect is largely attributable to CD24 function. Since Fc protein often exacerbated arthritis (data not shown), vehicle controls were used for in vivo studies to avoid inducing a confounding effect.

Therapeutic Effect of CD24Fc in Collagen-Induced Arthritis (CIA) Models

Figure 13A:
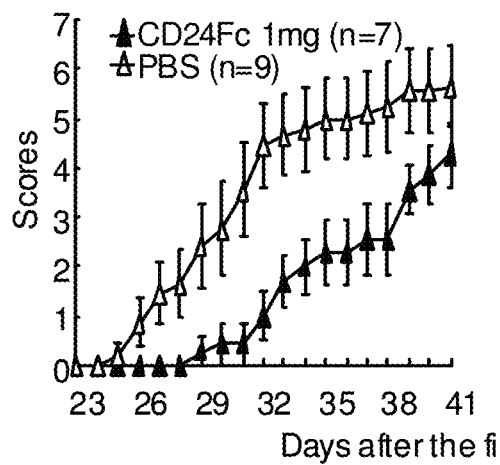
FIGS. 13A-B. CD24Fc conferred protection against CIA in DBA/1 mice.
Figure 13B:
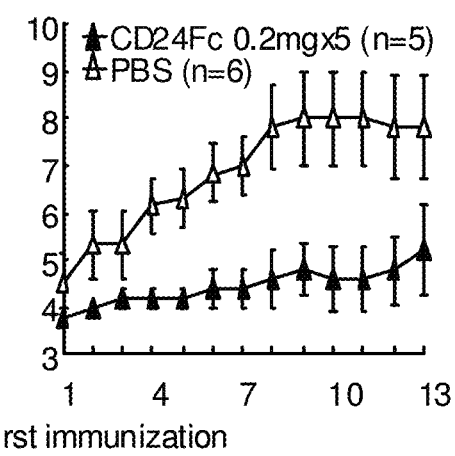

Since CAIA primarily reflects joint inflammation initiated by antibody-induced tissue injuries, and since RA involves both adaptive and innate immune-mediated destruction that can be better reflected in CIA setting, two CIA models were used to study to potential therapeutic effect of the CD24Fc. First, the prophylactic effect of CD24Fc were tested in the DBA/1 mouse. As shown in FIG. 13A, treatment with a single dose of CD24Fc prior to the development of clinical symptoms substantially reduced subsequent disease scores (P=0.02). To determine whether CD24Fc confers therapeutic effect for ongoing CIA in the DBA/1 mice, the treatment was initiated when the mice had arthritis scores from 3 to 8. The CD24Fc (200 μg/mouse) or vehicle was delivered every other day for 5 times. As shown in FIG. 13B, a clear reduction of arthritis score was observed as early as after two treatments. Significant reduction of clinical symptoms was observed in the CD24Fc group (P=0.02).

Figure 14A:
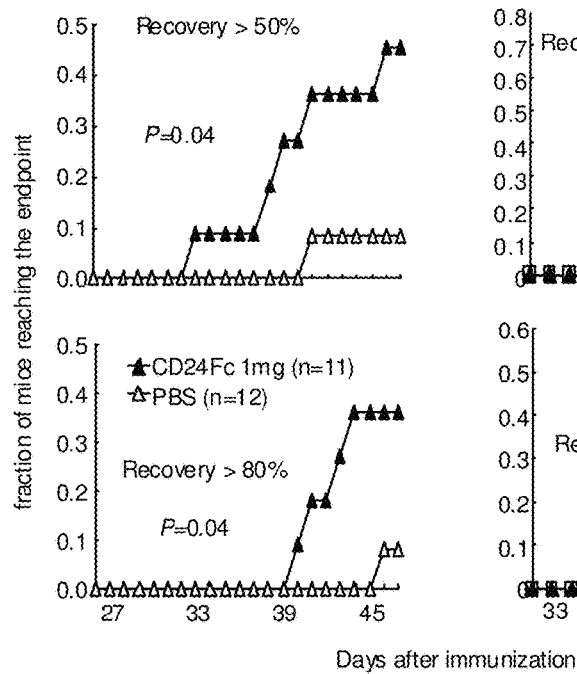
FIGS. 14A-B. CD24Fc caused rapid recovery in mice with ongoing chicken CIA. On day 1, 8-week old C57BL/6 mice were immunized with 100 µL of collagen-CFA emulsion (made by mixing 4 mg/ml of chick type II collagen with equal volume of CFA containing 5 mg/ml of M. tuberculosis) intradermally at the base of the tail. On day 21, booster immunization with the same collagen-CFA emulsion was administered intradermally 1.5 cm from the tail base.
Figure 14B:
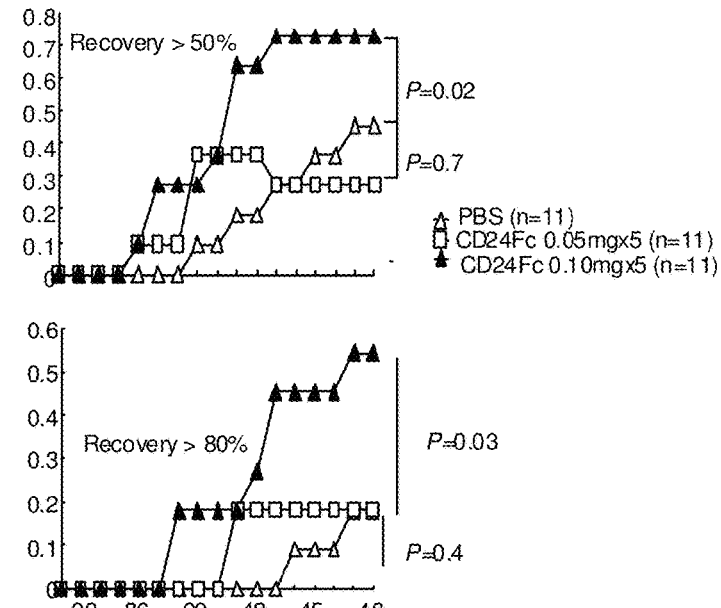

It has been reported that chicken collagen induces severe arthritis in C57BL/6 background. Therefore, this model was used to substantiate the therapeutic effect of CD24Fc. Since a significant variation in disease score was observed within the same group, 50% and 80% reductions of disease scores were used as the endpoints of the study. The percentage of mice that reached either therapeutic endpoint over a three week period was compared. As shown in FIG. 14A, CD24Fc accelerated recovery of mice after severe clinical signs had developed. To test the therapeutic effect at the peak of diseases, another week was allowed to pass for mice to reach peak clinical score, at which point mice were treated with repeated injections of either 100 or 50 μg/mouse (once every other day for a total of 5 injections). As shown in FIG. 14B, a transient increase of recovery was achieved with 50 μg/mouse/injection. However, a sustained recovery was achieved with only 100 m/mouse/injection. These data demonstrate a dose-dependent therapeutic effect even when the drug was administered at the peak of diseases.

CD24Fc Inhibits Production of Inflammatory Cytokines by a Human Macrophage Cell Line with shRNA Silencing of CD24

Figures 15A, 15B, 15C:
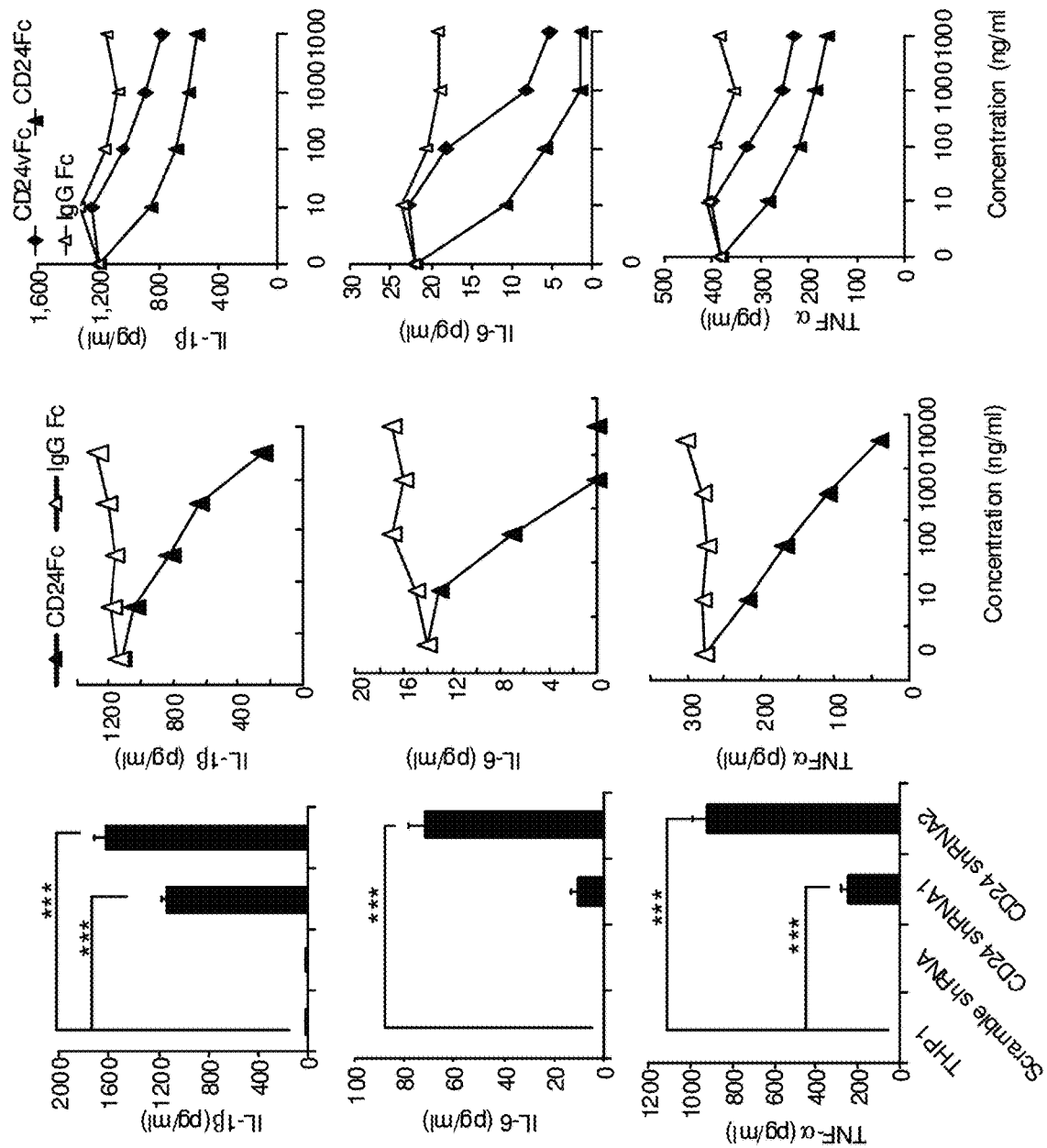
FIGS. 15A-C. CD24 inhibited inflammatory cytokine production by human macrophages.

To determine whether CD24 regulates production of inflammatory cytokines in human cell line, CD24 was silenced in human THP1 cell line and then differentiation into macrophage was induced by treating the cells with PMA. As shown in FIG. 15A, CD24 silencing substantially increased production of TNFα, IL-1β, and IL-6. These data demonstrate an essential role for endogenous human CD24 in production of inflammatory cytokines. Importantly, CD24Fc strongly inhibited production of TNFα, as well as IL-1β and IL-6 (FIG. 15B). Consistent with the therapeutic effect in vivo, CD24$^V$Fc was approximately 10-fold less effective in inhibiting the production of inflammatory cytokines in the macrophage cell line (FIG. 15C).

CD24Fc Confers Protection by Signaling Through Siglec G

Figure 16A:
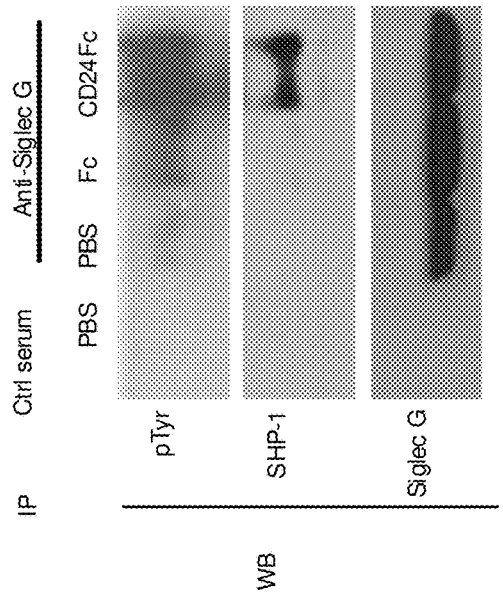
FIGS. 16A-C. Contribution of Siglec G to protection by CD24Fc.

It has been reported that CD24Fc interacts with Siglec G in mice and Siglec 10 in humans. To determine whether CD24Fc signals through Siglec G, spleen cells from CD24$^{-/-}$ mice were incubated with either vehicle, Fc or CD24Fc for 30 min, and tyrosine phosphorylation and SHP-1 binding to Siglec G were measured. As shown in FIG. 16A, CD24Fc strongly stimulated tyrosine phosphorylation of Siglec G. Correspondingly, the amount of SHP1 co-precipitated with Siglec G was dramatically increased. These results demonstrate that CD24Fc is capable of signaling through Siglec G.

Figure 16B:
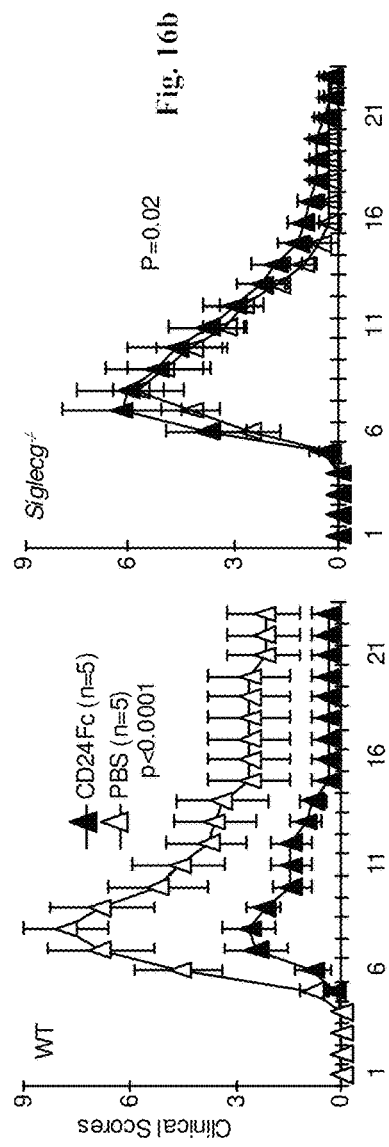
Figure 16C:
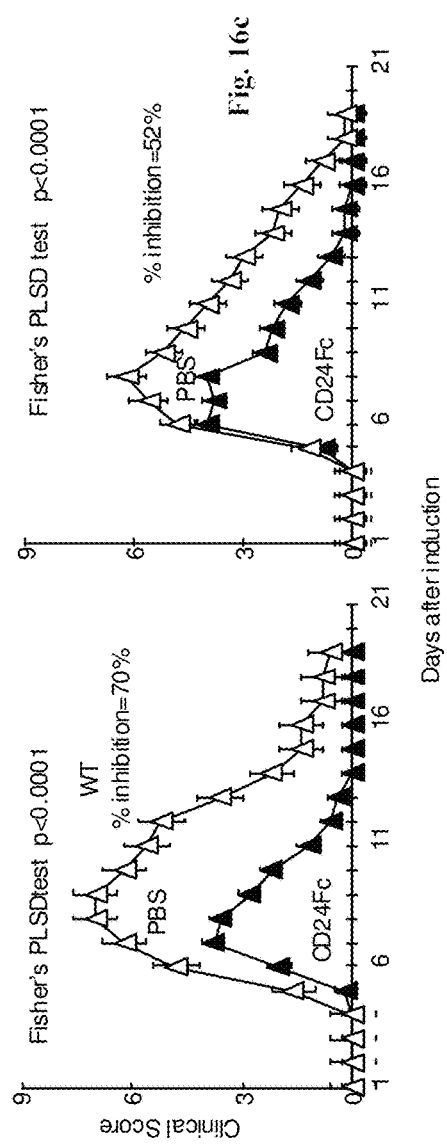

To test the significance of CD24Fc signaling through Siglec G in therapy of RA, WT mice and Siglec G-deficient mice were compared for their response to CD24Fc. As shown in FIG. 16B, when lower doses of anti-collagen antibodies were used, disease was less severe, yet the protection was completely dependent on the Siglecg gene. However, with increased doses of anti-collagen antibodies, the protective effect was only partially dependent on Siglecg, as the protection was still obvious, albeit less pronounced (52% in KO vs 72% in WT mice) (FIG. 16C). These data demonstrate that while CD24Fc can signal through Siglec G to confer protection against CAIA, an additional mechanism exists that allows CD24Fc to protect against RA in the absence of Siglec G.

Discussion

Taken together, the results demonstrate that CD24Fc has potent therapeutic effects in three mouse RA models, including a CAIA and two CIA models. The efficacies in multiple models indicates that CD24Fc has a therapeutic effect among RA in humans with different underlying pathogenesis. For decades, it has been assumed that RA is predominantly a T-cell mediated autoimmune diseases. In the last two decades, there has been a re-awaking on the possible role for antibodies and B lymphocytes in RA pathogenesis. Thus, in addition to rheumatoid factors, a host of autoantibodies have been found in RA patients. Several lines of evidence have demonstrated that in the mouse models, antibodies specific for either ubiquitous or tissue specific antigens are sufficient to cause RA symptoms. For instance, antibodies from K/BxN TCR transgenic mice were found to be fully capable of transferring RA-like diseases in the new host. Likewise, a cocktail of 4 anti-collagen antibodies is now widely used to induce RA in mice. Genetic analyses of the CAIA model indicate critical roles for complement. Although other possibilities exist, these requirements suggest potential involvement of antibody-mediated tissue damage in the pathogenesis of RA. The efficacy of CD24Fc in this model demonstrates that the fusion protein may be useful for antibody-mediated destruction phase in RA patients.

The CIA model is commonly used for RA as it can mimic both induction and effector function of both adaptive and innate immunity. Two CIA models were used to validate the therapeutic effect of CD24Fc. Bovine collagen-induced RA in DBA/1 mice is the most commonly used model. The above data show that CD24Fc reduced the disease score either before or after onset of disease in this model. One drawback of the bovine CIA model is that only relatively small numbers of strains are susceptible. In particular, C57BL/6 mice, which are commonly used for genetic studies are resistant. More recently, a protocol has been developed to induce CIA in C57BL/6 mice using chicken collagen. As shown above, CD24Fc accelerated recovery of arthritis induced by chicken collagen. The fact that the CD24Fc confers protection in multiple models demonstrates the robustness of its therapeutic effect.

An important issue relating to drug development is mechanism of action. Since it has been reported that CD24Fc binds to both Siglec G and human Siglec 10, the significance of this interaction was evaluated. In vitro, as shown above, CD24Fc signals through Siglec G and triggers tyrosine phosphorylation. In vivo, as shown above, CD24Fc works at least in part through Siglec G. These results demonstrate that it is plausible that CD24Fc protects against RA through strengthening the Siglec G-mediated protection against innate immunity to DAMPs. To date, no RA drug has been developed by fortifying the negative regulation over innate response to DAMPs. Therefore, CD24Fc and other fusion proteins containing variant CD24 missing the polymorphic A/V amino acid (SEQ ID NO: 1) represents a new class of therapeutics for RA. This approach may be preferable to antibodies targeting individual DAMPs or inflammatory cytokines. Since multiple DAMPs are released during autoimmune destruction, targeting individual DAMP may be less effective than targeting a broad-spectrum regulator such as CD24-Siglec G pathway. Nevertheless, it should be pointed out that the data in this example demonstrate that the protection is not completely dependent on signaling through Siglec G. At least two additional mechanisms can be invoked. First, by binding to DAMPs, CD24 may reduce the amounts of DAMPs available for their agonist receptors, such as RAGE, TLR. Second, since CD24 is heterogeneously glycosylated, it may bind to other members of Siglecs to confer negative regulation.

CONCLUSION

A fusion protein comprising a non-polymorphic extracellular domain of human CD24 (comprising SEQ ID NO: 1)

protects mice against arthritis initiated by either anti-collagen antibodies or immunization of collagen. The protection is at least partially dependent on its interaction with Siglec G. The data demonstrate the potential of harnessing the negative regulation of innate immunity to tissue injuries. Unexpectedly, the non-polymorphic variant of CD24 is superior to wild-type CD24 in suppressing inflammatory cytokine production and protecting mice against RA.

The invention claimed is:

1. A method of treating multiple sclerosis (MS) in a human subject in need thereof, comprising administering to the subject a CD24 protein comprising a mature human CD24 polypeptide, wherein the sequence of the mature human CD24 polypeptide comprises the sequence set forth in SEQ ID NO: 1, wherein the CD24 protein does not comprise an alanine or valine immediately C-terminal to SEQ ID NO: 1, and wherein a Fc portion of a human Ig protein is fused to the C-terminus of the mature human CD24 polypeptide.

2. The method of claim 1, wherein the Fc portion comprises (a) a hinge region and CH2 and CH3 domains of the human Ig protein, wherein the human Ig protein is selected from the group consisting of IgG1, IgG2, IgG3, IgG4, and IgA; or (b) a hinge region and CH$_3$ and CH$_4$ domains of IgM.

3. The method of claim 1, wherein the sequence of the CD24 protein consists of the sequence set forth in SEQ ID NO: 1 fused at the C-terminus to the hinge region and CH2 and CH3 domains of human IgG1 Fc.

4. The method of claim 3, wherein the sequence of the hinge region and CH2 and CH3 domains of human IgG1 Fc consists of the sequence set forth in SEQ ID NO: 6.

5. The method of claim 1, wherein the CD24 protein is produced using a eukaryotic protein expression system.

6. The method of claim 5, wherein the expression system comprises a vector contained in a Chinese Hamster Ovary cell line or a replication-defective retroviral vector.

7. The method of claim 1, wherein the treating comprises repressing an immune response to autoimmune tissue destruction.

8. The method of claim 7, wherein the treating comprises repressing tissue damage.

9. The method of claim 7, wherein the immune response is mediated by danger-associated molecular patterns.

10. A method of treating MS in a subject in need thereof, comprising administering to the subject a CD24 protein, wherein the amino acid sequence of the CD24 protein consists of the sequence set forth in SEQ ID NO: 1 fused at its C-terminus to a hinge region and CH2 and CH3 domains of human IgG1.

11. The method of claim 10, wherein the amino acid sequence of the hinge region and CH2 and CH3 domains of human IgG1 consist of the sequence set forth in SEQ ID NO: 6.

12. The method of claim 10, wherein the treating comprises repressing an immune response to autoimmune tissue destruction.

13. The method of claim 12, wherein the treating comprises repressing tissue damage.

14. The method of claim 10, wherein the immune response is mediated by danger-associated molecular patterns.

* * * * *

SEQUENCE LISTING

```
<160> NUMBER OF SEQ ID NOS: 7

<210> SEQ ID NO 1
<211> LENGTH: 30
<212> TYPE: PRT
<213> ORGANISM: Homo sapiens

<400> SEQUENCE: 1

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30

<210> SEQ ID NO 2
<211> LENGTH: 31
<212> TYPE: PRT
<213> ORGANISM: Homo sapiens
<220> FEATURE:
<221> NAME/KEY: Xaa
<222> LOCATION: (31)..(31)
<223> OTHER INFORMATION: Val or Ala

<400> SEQUENCE: 2

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Xaa
            20                  25                  30

<210> SEQ ID NO 3
<211> LENGTH: 27
<212> TYPE: PRT
<213> ORGANISM: Mus musculus

<400> SEQUENCE: 3

Asn Gln Thr Ser Val Ala Pro Phe Pro Gly Asn Gln Asn Ile Ser Ala
1               5                   10                  15

Ser Pro Asn Pro Thr Asn Ala Thr Thr Arg Gly
            20                  25

<210> SEQ ID NO 4
<211> LENGTH: 26
<212> TYPE: PRT
<213> ORGANISM: Homo sapiens

<400> SEQUENCE: 4

Met Gly Arg Ala Met Val Ala Arg Leu Gly Leu Gly Leu Leu Leu Leu
1               5                   10                  15

Ala Leu Leu Leu Pro Thr Gln Ile Tyr Ser
            20                  25

<210> SEQ ID NO 5
<211> LENGTH: 287
<212> TYPE: PRT
<213> ORGANISM: Artificial Sequence
<220> FEATURE:
<223> OTHER INFORMATION: Human CD24 IgG1 Fc fusion

<400> SEQUENCE: 5

Met Gly Arg Ala Met Val Ala Arg Leu Gly Leu Gly Leu Leu Leu Leu
```

```
            1               5                  10                 15
          Ala Leu Leu Leu Pro Thr Gln Ile Tyr Ser Ser Glu Thr Thr Thr Gly
                       20                  25                 30

Thr Ser Ser Asn Ser Ser Gln Ser Thr Ser Asn Ser Gly Leu Ala Pro
                       35                  40                 45

Asn Pro Thr Asn Ala Thr Thr Lys Pro Lys Ser Cys Asp Lys Thr His
           50                  55                 60

Thr Cys Pro Pro Cys Pro Ala Pro Glu Leu Leu Gly Gly Pro Ser Val
          65                  70                 75                 80

Phe Leu Phe Pro Pro Lys Pro Lys Asp Thr Leu Met Ile Ser Arg Thr
                              85                 90                 95

Pro Glu Val Thr Cys Val Val Val Asp Val Ser His Glu Asp Pro Glu
                         100                 105                110

Val Lys Phe Asn Trp Tyr Val Asp Gly Val Glu Val His Asn Ala Lys
                         115                 120                125

Thr Lys Pro Arg Glu Glu Gln Tyr Asn Ser Thr Tyr Arg Val Val Ser
                         130                 135                140

Val Leu Thr Val Leu His Gln Asp Trp Leu Asn Gly Lys Glu Tyr Lys
          145                 150                 155                160

Cys Lys Val Ser Asn Lys Ala Leu Pro Ala Pro Ile Glu Lys Thr Ile
                              165                 170                175

Ser Lys Ala Lys Gly Gln Pro Arg Glu Pro Gln Val Tyr Thr Leu Pro
                         180                 185                 190

Pro Ser Arg Asp Glu Leu Thr Lys Asn Gln Val Ser Leu Thr Cys Leu
                         195                 200                 205

Val Lys Gly Phe Tyr Pro Ser Asp Ile Ala Val Glu Trp Glu Ser Asn
          210                 215                 220

Gly Gln Pro Glu Asn Asn Tyr Lys Thr Thr Pro Pro Val Leu Asp Ser
          225                 230                 235                240

Asp Gly Ser Phe Phe Leu Tyr Ser Lys Leu Thr Val Asp Lys Ser Arg
                         245                 250                 255

Trp Gln Gln Gly Asn Val Phe Ser Cys Ser Val Met His Glu Ala Leu
                         260                 265                 270

His Asn His Tyr Thr Gln Lys Ser Leu Ser Leu Ser Pro Gly Lys
                         275                 280                 285

<210> SEQ ID NO 6
<211> LENGTH: 231
<212> TYPE: PRT
<213> ORGANISM: Homo sapiens

<400> SEQUENCE: 6

Pro Lys Ser Cys Asp Lys Thr His Thr Cys Pro Pro Cys Pro Ala Pro
1               5                  10                 15

Glu Leu Leu Gly Gly Pro Ser Val Phe Leu Phe Pro Pro Lys Pro Lys
            20                  25                 30

Asp Thr Leu Met Ile Ser Arg Thr Pro Glu Val Thr Cys Val Val Val
        35                  40                 45

Asp Val Ser His Glu Asp Pro Glu Val Lys Phe Asn Trp Tyr Val Asp
    50                  55                 60

Gly Val Glu Val His Asn Ala Lys Thr Lys Pro Arg Glu Glu Gln Tyr
65                  70                 75                 80

Asn Ser Thr Tyr Arg Val Val Ser Val Leu Thr Val Leu His Gln Asp
                85                  90                 95
```

```
Trp Leu Asn Gly Lys Glu Tyr Lys Cys Lys Val Ser Asn Lys Ala Leu
                100                 105                 110
Pro Ala Pro Ile Glu Lys Thr Ile Ser Lys Ala Lys Gly Gln Pro Arg
            115                 120                 125
Glu Pro Gln Val Tyr Thr Leu Pro Pro Ser Arg Asp Glu Leu Thr Lys
        130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
210                 215                 220
Leu Ser Leu Ser Pro Gly Lys
225                 230
```

<210> SEQ ID NO 7
<211> LENGTH: 288
<212> TYPE: PRT
<213> ORGANISM: Artificial
<220> FEATURE:
<223> OTHER INFORMATION: CD24VFc

<400> SEQUENCE: 7

```
Met Gly Arg Ala Met Val Ala Arg Leu Gly Leu Gly Leu Leu Leu Leu
1               5                   10                  15
Ala Leu Leu Leu Pro Thr Gln Ile Tyr Ser Ser Glu Thr Thr Thr Gly
            20                  25                  30
Thr Ser Ser Asn Ser Ser Gln Ser Thr Ser Asn Ser Gly Leu Ala Pro
        35                  40                  45
Asn Pro Thr Asn Ala Thr Thr Lys Val Pro Lys Ser Cys Asp Lys Thr
50                  55                  60
His Thr Cys Pro Pro Cys Pro Ala Pro Glu Leu Leu Gly Gly Pro Ser
65                  70                  75                  80
Val Phe Leu Phe Pro Pro Lys Pro Lys Asp Thr Leu Met Ile Ser Arg
                85                  90                  95
Thr Pro Glu Val Thr Cys Val Val Val Asp Val Ser His Glu Asp Pro
            100                 105                 110
Glu Val Lys Phe Asn Trp Tyr Val Asp Gly Val Glu Val His Asn Ala
        115                 120                 125
Lys Thr Lys Pro Arg Glu Glu Gln Tyr Asn Ser Thr Tyr Arg Val Val
        130                 135                 140
Ser Val Leu Thr Val Leu His Gln Asp Trp Leu Asn Gly Lys Glu Tyr
145                 150                 155                 160
Lys Cys Lys Val Ser Asn Lys Ala Leu Pro Ala Pro Ile Glu Lys Thr
                165                 170                 175
Ile Ser Lys Ala Lys Gly Gln Pro Arg Glu Pro Gln Val Tyr Thr Leu
            180                 185                 190
Pro Pro Ser Arg Asp Glu Leu Thr Lys Asn Gln Val Ser Leu Thr Cys
        195                 200                 205
Leu Val Lys Gly Phe Tyr Pro Ser Asp Ile Ala Val Glu Trp Glu Ser
210                 215                 220
```

-continued

```
Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
            245                 250                 255

Arg Trp Gln Gln Gly Asn Val Phe Ser Cys Ser Val Met His Glu Ala
        260                 265                 270

Leu His Asn His Tyr Thr Gln Lys Ser Leu Ser Leu Ser Pro Gly Lys
        275                 280                 285
```